(12) United States Patent
Sabelle et al.

(10) Patent No.: US 11,504,318 B2
(45) Date of Patent: Nov. 22, 2022

(54) SYMMETRIC AZOMETHINE DIRECT DYES, PROCESS FOR THEIR PREPARATION, COSMETIC COMPOSITION COMPRISING AT LEAST ONE SUCH DYE AND USE THEREOF

(71) Applicant: L'OREAL, Paris (FR)

(72) Inventors: Stéphane Sabelle, Aulnay-Sous-Bois (FR); Stéphane Blais, Aulnay-Sous-Bois (FR); Aziz Fadli, Aulnay-Sous-Bois (FR)

(73) Assignee: L'OREAL, Paris (FR)

( * ) Notice: Subject to any disclaimer, the term of this patent is extended or adjusted under 35 U.S.C. 154(b) by 13 days.

(21) Appl. No.: 16/467,591

(22) PCT Filed: Dec. 15, 2017

(86) PCT No.: PCT/EP2017/082989
§ 371 (c)(1),
(2) Date: Jun. 7, 2019

(87) PCT Pub. No.: WO2018/109156
PCT Pub. Date: Jun. 21, 2018

(65) Prior Publication Data
US 2022/0016009 A1 Jan. 20, 2022

(30) Foreign Application Priority Data
Dec. 16, 2016 (FR) ..................................... 1662657

(51) Int. Cl.
*A61Q 5/10* (2006.01)
*A61K 8/49* (2006.01)
(Continued)

(52) U.S. Cl.
CPC ............ *A61K 8/4946* (2013.01); *A61K 8/415* (2013.01); *A61K 8/466* (2013.01); *C09B 55/002* (2013.01);
(Continued)

(58) Field of Classification Search
CPC ...... A61Q 5/065; A61K 8/4946; A61K 8/416; A61K 2800/5426; A61K 8/415; A61K 8/466; A61K 2800/4322; C09B 55/002
(Continued)

(56) References Cited

U.S. PATENT DOCUMENTS 3,518,234 A * 6/1970 Tsunemasa ............ C08G 73/18
525/435
3,853,464 A 12/1974 Kalopissis et al.
(Continued)

FOREIGN PATENT DOCUMENTS

DE 2359399 A1 6/1975
DE 3843892 A1 6/1990
(Continued)

OTHER PUBLICATIONS

STIC Search Report dated Jan. 10, 2022.*
International Search Report and Written Opinion for counterpart Application No. PCT/EP2017/08289, dated Apr. 4, 2018.
International Search Report and Written Opinion for counterpart Application No. PCT/EP2017/082985, dated Apr. 4, 2018.
Boydston, Andrew J. et al., "Modular Fluorescent Benzobis(imidazolium) Salts: Syntheses, Photophysical Analyses, and Applications," XP055282021, Journal of the American Chemical Society, vol. 130, No. 10, Mar. 1, 2008, pp. 3143-3156.
(Continued)

*Primary Examiner* — Eisa B Elhilo
(74) *Attorney, Agent, or Firm* — The Marbury Law Group, PLLC

(57) ABSTRACT

The present invention relates to a process for dyeing keratin fibres, in particular human keratin fibres such as the hair, in one or more steps, comprising the application to said keratin fibres of a composition comprising one or more compounds of formula (I) and/or (II), and also to the use thereof for dyeing keratin fibres, and to a device: in which formula (I) or (II) $R_1$, $R_3$, $R_4$, $R_5$, $R_6$, and n are as defined in the description. The compounds of formula (I) according to the invention can give powerful, chromatic and sparingly selective colourings with good colour build-up, which are resistant to the various attacking factors to which keratin fibres may be subjected, such as inclement weather, light, washing and perspiration.

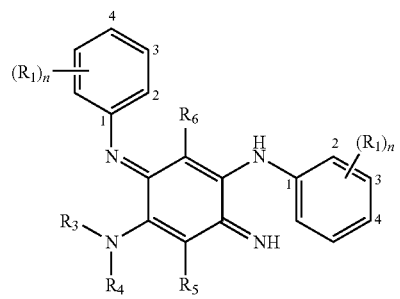

(I)

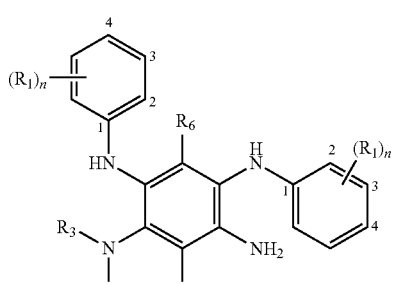

(II)

17 Claims, No Drawings

(51) Int. Cl.
*A61K 8/41* (2006.01)
*A61K 8/46* (2006.01)
*C09B 55/00* (2006.01)

(52) U.S. Cl.
CPC .. *A61K 2800/4322* (2013.01); *A61K 2800/88* (2013.01)

(58) Field of Classification Search
USPC .............................................................. 8/426
See application file for complete search history.

(56) References Cited

U.S. PATENT DOCUMENTS

| | | | |
|---|---|---|---|
| 3,884,625 | A | 5/1975 | Kalopissis et al. |
| 4,003,699 | A | 1/1977 | Rose et al. |
| 4,054,147 | A | 10/1977 | Kalopissis et al. |
| RE30,199 | E | 1/1980 | Rose et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Möckli |
| 5,766,576 | A | 6/1998 | Löwe et al. |
| 6,099,592 | A | 8/2000 | Vidal et al. |
| 6,284,003 | B1 | 9/2001 | Rose et al. |
| 6,730,789 | B1 | 5/2004 | Birault et al. |
| 8,066,782 | B2 * | 11/2011 | Leduc ................... C07D 401/04 8/405 |
| 8,083,809 | B2 * | 12/2011 | Leduc ................... C07C 251/22 8/405 |
| 8,105,394 | B2 * | 1/2012 | Leduc ................... A61K 8/4946 8/405 |
| 9,226,883 | B2 | 1/2016 | Sabelle et al. |
| 9,554,977 | B2 | 1/2017 | Sabelle et al. |
| 2011/0041261 | A1 * | 2/2011 | Leduc ................... C07D 403/04 8/426 |
| 2011/0041262 | A1 * | 2/2011 | Leduc ................... C07D 401/14 8/426 |
| 2011/0041263 | A1 * | 2/2011 | Leduc ................... C07D 207/14 8/426 |
| 2013/0269120 | A1 | 10/2013 | Lalleman et al. |

FOREIGN PATENT DOCUMENTS

| | | |
|---|---|---|
| DE | 4133957 A1 | 4/1993 |
| DE | 19543988 A1 | 5/1997 |
| EP | 0714954 A2 | 6/1996 |
| EP | 0770375 A1 | 5/1997 |
| EP | 2842949 A1 | 3/2015 |
| FR | 2047932 A1 | 3/1971 |
| FR | 2056799 A5 | 5/1971 |
| FR | 2165965 A1 | 8/1973 |
| FR | 2262023 A1 | 9/1975 |
| FR | 2733749 A1 | 11/1996 |
| FR | 2801308 A1 | 5/2001 |
| FR | 2886136 A1 | 12/2006 |
| FR | 2968947 A1 | 6/2012 |
| FR | 2983855 A1 | 6/2013 |
| FR | 2983856 A1 | 6/2013 |
| FR | 3006180 * 12/2014 | ............. A61Q 5/10 |
| GB | 1026978 A | 4/1966 |
| GB | 1153196 A | 5/1969 |
| JP | 02-019576 A | 1/1990 |
| JP | 05-163124 A | 6/1993 |
| KR | 10-2014-0060247 A | 5/2014 |
| WO | 96/15765 A1 | 5/1966 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 2018/109153 A1 | 6/2018 |

OTHER PUBLICATIONS

Fries, K., et al., "III. Untersuchungen in der Reihe des N-Phenyl—Azimidobenzols," XP055361572, Justus Liebigs AnnalenDer Chemie, vol. 389, No. 3, Jan. 1, 1912, pp. 345-367.

Jois, E.H. et al., "Isomerisation of Benzylidene Derivatives. Part I," XP009194012, Journal of the Indian Chemical Society, The Indian Chemical Society, Calcutta, IN, vol. 16, Jan. 1939, pp. 43-46.

Kane, James J. et al., "Synthesis of New Nitrogen Substituted Polybenzimidazoles," XP055361543, MRS Proceedings, vol. 134, Jan. 1, 1988, pp. 135-136 and p. 138.

Ko, Hye Jin, et al., "Organic Light Emitting Device Comprising Novel Nitrogen-Bearing Electron Transport Material," XP002759032, Chemical Abstracts Service, Columbus, OH, Database Accession No. 2014:821808, Abstract.

Liu, Binna et al., "Systematic Evaluation of Structure-Activity Relationships of the Riminophenazine Class and Discovery of a C2 Pyridylamino Series for the Treatment of Multidrug-Resistant Tuberculosis," XP055361456, Molecules, vol. 17, No. 12, Apr. 17, 2012, pp. 4545-4559.

Nietzki, R., et al., "Synthese von Symmetrischem Tetramidobenzol Mittels Dinitrochlorbenzol," XP055361638, Berichte Der Deutschen Chemischen Gesellschaft, vol. 30, No. 2, Jan. 1, 1897, pp. 1666-1669.

Vogel, H., et al., "Polybenzimidazoles. II," XP002290993, Journal of Polymer Science, Part A: Polymer Chemistry, John Wiley & Sons, Inc., vol. 1, Jan. 1, 1963, pp. 1531-1541.

Non-Final Office Action for copending U.S. Appl. No. 16/467,352, dated Jul. 1, 2020.

STIC Search Report dated May 26, 2020.

* cited by examiner

SYMMETRIC AZOMETHINE DIRECT DYES, PROCESS FOR THEIR PREPARATION, COSMETIC COMPOSITION COMPRISING AT LEAST ONE SUCH DYE AND USE THEREOF

CROSS REFERENCE TO RELATED APPLICATIONS

This is a national stage application of PCT/EP2017/082989, filed internationally on Dec. 15, 2017, which claims priority to French Application No. 1662657, filed on Dec. 16, 2016, both of which are incorporated by reference herein in their entireties.

The present invention relates to a process for dyeing keratin fibres, in particular human keratin fibres such as the hair, in one or more steps, comprising the application to said keratin fibres of a composition comprising one or more compounds of formula (I) and/or the leuco forms thereof of formula (II), and also to the use of one or more compounds of formula (I) and/or (II) for dyeing keratin fibres, and to a device therefor.

It is known practice to dye keratin fibres, and in particular the hair, with cosmetic compositions containing one or more direct dyes, according to a "direct dyeing" process.

The process conventionally used in direct dyeing consists in applying to keratin fibres one or more direct dyes, or colouring molecules, which have affinity for said fibres, leaving them to stand on the fibres, and then rinsing the fibres. The direct dyes used hitherto are generally nitrobenzene dyes, anthraquinone dyes, nitropyridine dyes, dyes of azo, xanthene, acridine or azine type or triarylmethane-based dyes.

However, the colourings that result therefrom are temporary or semi-permanent, since the nature of the interactions that bind the direct dyes to the keratin fibre and their desorption from the surface and/or the core of the fibre are responsible for their weak dyeing power and their poor fastness with respect to washing, inclement weather or perspiration.

These dyes may also have the drawback of lacking in stability towards light, on account of the poor resistance of the chromophore to photochemical attack, which has a tendency to lead to fading over time of the colouring of the keratin fibres and/or to change in the colour.

In addition, although a wide range of colours is currently accessible, it generally proves necessary to combine three dyes of complementary colours—trichromatic principle—in order to obtain a natural chestnut-brown, dark chestnut-brown, brown or black shade (see, for example, WO 95/15144 and WO 95/101772). This tripartite combination does not, however, show good persistence with respect to repeated shampooing. It generally, or even systematically, induces an unaesthetic changing of the colour, which the consumer finds dissuasive.

There is thus a real need for direct dyes that can dye keratin fibres in an intense, chromatic manner with good build-up of the colour, which are stable towards light, and/or capable of giving colourings that are resistant to the various attacking factors to which the fibres may be subjected, such as inclement weather, washing and perspiration.

A particular aim of the present invention is also to be able to dye light keratin fibres efficiently chestnut-brown, dark chestnut-brown, brown or brown with a glint or even black, with a single type of dye of formula (I) or (II) as defined below.

These aims are achieved with the present invention, one subject of which is especially a process for dyeing keratin fibres, in particular human keratin fibres such as the hair, in one or more steps, comprising the application to said keratin fibres of a composition comprising one or more compounds of formula (I) and/or (II) below, organic or mineral acid or base salts thereof, tautomeric forms, optical isomers or geometrical isomers thereof and/or solvates thereof:

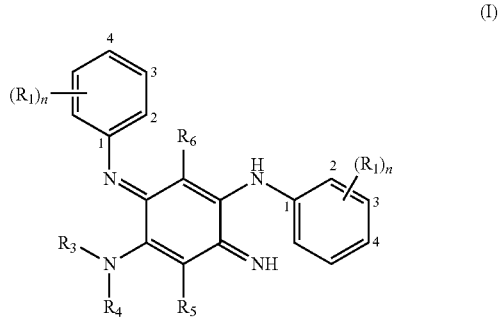

(I)

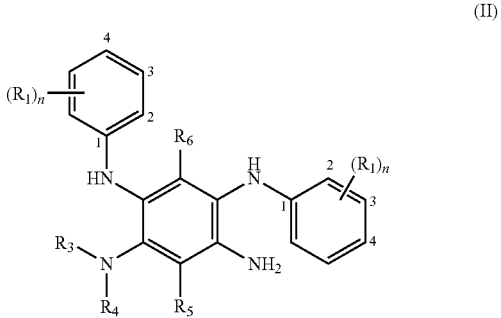

(II)

in which formulae (I) and (II):

n represents an integer equal to 0, 1, 2, 3, 4 or 5; preferably, n represents 0 or 1;

$R_1$ represents:

a halogen atom;

a sulfonic radical —$SO_3H$ or sulfonate radical —$SO_3^-$;

a carboxyl radical —$CO_2H$, a carboxylate radical —$COO^-$;

an aromatic or non-aromatic, 5- to 10-membered cationic heterocycle, which is optionally substituted, especially with one or more identical or different radicals chosen from $C_1$-$C_4$ alkyl and $C_1$-$C_4$ hydroxyalkyl;

an aromatic or non-aromatic, 5- to 6-membered non-cationic heterocycle, substituted with:

an ammonium radical —$N^+RR'R''$ with R, R' and R", which may be identical or different, representing a ($C_1$-$C_4$)alkyl group optionally substituted with one or more hydroxyl groups, such as methyl, ethyl, propyl or 2-hydroxyethyl, and/or an aromatic or non-aromatic, 5- to 10-membered cationic heterocycle, which is optionally substituted, especially with one or more identical or different radicals chosen from $C_1$-$C_4$ alkyl and $C_1$-$C_4$ hydroxyalkyl, an ammonium radical —N⁺RR'R" with R, R' and R" as defined previously, and preferably R, R' and R", which may be identical or different, represent a $C_1$-$C_4$ alkyl group such as methyl, or a radical W—$R_7$, in which:
  W represents:
    an oxygen or sulfur atom,
    a divalent group —N($R_8$)— or
    a linear or branched, saturated or unsaturated, preferably saturated, divalent hydrocarbon-based chain, comprising from 1 to 14 carbon atoms, said hydrocarbon-based chain being:
      optionally substituted with one or more radicals, which may be identical or different, chosen from the following radicals: i) hydroxyl, ii) (di)($C_1$-$C_6$) (alkyl)amino, iii) ammoniums —N⁺RR'R" with R, R' and R" as defined previously, iv) aromatic or non-aromatic, optionally substituted, 5- to 10-membered cationic heterocycles, preferably a 5- or 6-membered cationic heteroaryl optionally substituted with one or more ($C_1$-$C_4$)alkyl groups, such as ($C_1$-$C_4$)(alkyl)imidazolium, v) aromatic or non-aromatic, 5- or 6-membered non-cationic heterocycles, substituted with one or more radicals, which may be identical or different, chosen from the following radicals: a) ammonium —N⁺RR'R" with R, R' and R" as defined previously, and b), aromatic or non-aromatic, 5- to 10-membered cationic heterocycle, optionally substituted especially with one or more identical or different radicals chosen from $C_1$-$C_4$ alkyl; preferably, the cationic heterocycle is a cationic heteroaryl optionally substituted with one or more ($C_1$-$C_4$)alkyl groups, such as ($C_1$-$C_4$)(alkyl)imidazolium;
      and/or
        optionally interrupted, optionally starting and/or optionally terminating with one or more divalent heteroatoms or groups, which may be identical or different, chosen from:
          —O—, —S—, —N($R_{10}$)—, —S(O)—, and —C(X)— with X representing an oxygen or sulfur atom or a group $NR_{10}$ and $R_{10}$ representing a hydrogen atom or a ($C_1$-$C_6$)alkyl group, and combinations thereof;
          preferably optionally interrupted, optionally starting and/or optionally terminating with: —O—, —N($R_{10}$)—, —O—C(O)—, —C(O)—O—, —C(O)—N(H)—, —N(H)—C(O)—, —N(H)—C(O)—N(H)—, —O—C(O)—N(H)—, —N(H)—C(O)—O—, or —N(H)—C(NH)—NH—;
  $R_7$ and $R_8$, which may be identical or different, represent:
    a hydrogen atom,
    a linear or branched $C_1$-$C_{14}$, in particular $C_1$-$C_8$ and preferably $C_1$-$C_6$ alkyl group, said alkyl group being:
      optionally interrupted with one or more heteroatoms or groups, which may be identical or different, such as —O—, —S—, —N($R_{10}$)—, —S(O)—, —S(O)$_2$— and —C(X)— with X and $R_{10}$ as defined previously, or combinations thereof; and/or
      optionally substituted with one or more radicals, which may be identical or different, chosen from the following radicals: i) hydroxyl, ii) (di)($C_1$-$C_6$)(alkyl)amino, iii) ammoniums —N⁺RR'R" with R, R' and R" as defined previously, iv) aromatic or non-aromatic, optionally substituted, 5- to 10-membered cationic heterocycles: preferably a 5- or 6-membered cationic heteroaryl optionally substituted with one or more ($C_1$-$C_4$)alkyl groups, such as ($C_1$-$C_4$)(alkyl)imidazolium, v) aromatic or non-aromatic, 5- or 6-membered non-cationic heterocycles, substituted with one or more radicals, which may be identical or different, chosen from the following radicals: a) ammonium —N⁺RR'R" with R, R' and R" as defined previously, and b), aromatic or non-aromatic, 5- to 10-membered cationic heterocycle, optionally substituted especially with one or more identical or different radicals chosen from alkyl; preferably, the cationic heterocycle is a cationic heteroaryl optionally substituted with one or more ($C_1$-$C_4$)alkyl groups, such as ($C_1$-$C_4$)(alkyl)imidazolium:

$R_3$ and $R_4$, which may be identical or different, representing:
  a hydrogen atom,
  a ($C_1$-$C_6$)alkyl radical optionally substituted with one or more radicals chosen from i) hydroxyl, ii) ($C_1$-$C_4$)alkoxy, iii) amino, iv) ($C_1$-$C_6$)alkylamino and v) di($C_1$-$C_6$)alkylamino;

$R_5$ and $R_6$, which may be identical or different, represent an atom or group chosen from:
  a hydrogen atom,
  a halogen atom,
  a $C_1$-$C_6$ alkyl radical,
  a ($C_1$-$C_6$)alkyl radical substituted with one or more radicals chosen from the following radicals: i) hydroxyl, ii) amino —NH$_2$, iii) ($C_1$-$C_6$)alkylamino, and iv) di($C_1$-$C_6$)alkylamino,
  a ($C_1$-$C_6$)alkoxy radical, and
  a ($C_1$-$C_6$)alkoxy radical substituted with one or more radicals chosen from the following radicals: i) hydroxyl, ii) amino, iii) ($C_1$-$C_6$)alkylamino, and iv) di($C_1$-$C_6$)alkylamino;

it being understood that:
  the compounds of formula (I) and (II) are symmetric,
  when the compound of formula (I) or (II) is cationic, it optionally comprises one or more anions An⁻ and optionally one or more cations M⁺ to ensure the electrical neutrality of the molecule; with:
    An⁻ denoting an anion, preferably chosen from bromide, chloride, methylsulfate and toluenesulfonate ions or a mixture of these ions;
    M⁺ representing a cation, preferably chosen from sodium, potassium, magnesium, calcium and ammonium Another subject of the present invention relates to the use of one or more azomethine direct dyes of formula (I), as defined previously, and/or of the leuco forms thereof (II) as defined below, optionally in the presence of one or more chemical oxidizing agents, for dyeing keratin fibres, in particular human keratin fibres such as the hair.

The present invention also relates to a cosmetic composition for dyeing keratin fibres, in particular human keratin fibres such as the hair, comprising one or more azomethine direct dyes of formula (I) and/or of the leuco forms thereof (II) as defined previously it being understood that the dye(s) of formula (I) are other than the following compound,

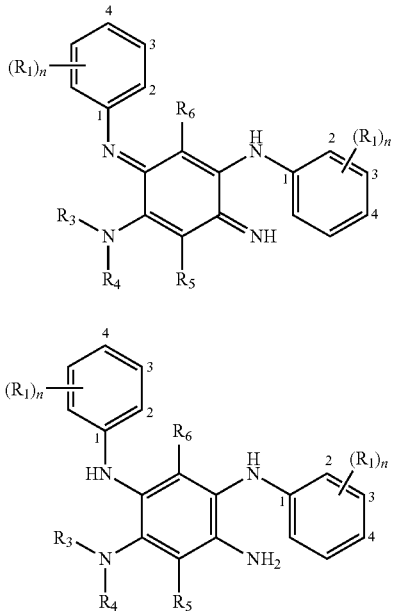

In particular, the invention also relates to the use of said cosmetic composition for dyeing keratin fibres, especially human keratin fibres such as the hair.

The process according to the invention can thus give colourings that are resistant to the various attacking factors to which keratin fibres may be subjected, such as inclement weather, light, washing and perspiration.

Furthermore, the process according to the invention can satisfactorily dye keratin fibres, especially producing powerful, chromatic and sparingly selective colourings, and/or colourings with good colour build-up.

It is known practice to use azomethine direct dyes for dyeing keratin fibres, but hese dyes are not always satisfactory in terms of the dyeing property.

The novel azomethine direct dyes of formula (I) or the direct dyeing precursors (II) have the feature of being symmetric and have the advantage of producing powerful and sparingly chromatic colours. Furthermore, it is possible to obtain natural colours, especially intense brown, dark brown, black or even green colours, on white keratin fibres using a single azomethine direct dye of formula (I) or a single direct dyeing precursor (II), without necessarily having to use a mixture of several direct dyes, or a mixture of several direct dyeing precursors, of complementary colours (trichromatic principle: see, for example, WO 95/15144 and WO 95/01772). The mixture of direct dyes has the drawback of not being stable with respect to light or washing, as a result of which unaesthetic changing of the colour is very often observed. Now, the dyes of the invention show good stability with respect to external agents such as light and washing once applied to the hair, and also good stability in an oxidizing medium.

Thus, the invention also relates to the use of one or more compounds of leuco type of formula (II) as precursors of the direct dyes of formula (I).

In particular, the invention relates to the use of one or more compounds of leuco type of formula (II) optionally in the presence of one or more chemical oxidizing agents, for dyeing keratin fibres, especially human keratin fibres such as the hair.

The compounds of leuco type of formula (II) used under oxidizing conditions thus have the advantage of giving colourings that are resistant to the various attacking factors to which keratin fibres may be subjected, such as inclement weather, washing, light or perspiration.

Moreover, the dyeing process using colourless or weakly coloured compounds of formuia (II) followed by a step of revealing the colour in the presence of a chemical oxidizing agent makes it possible to produce "clean" dyeing, i.e. dyeing that produces very little or no staining of clothing or linen such as towels used during said process.

The invention also relates to a single-compartment or multi-compartment device comprising a first compartment containing one or more compounds of formula (I) and/or (II), and a second compartment comprising one or more chemical oxidizing agents.

Other characteristics, aspects, subjects and advantages of the present invention will emerge even more clearly on reading the description and the examples that follow.

For the purposes of the invention, unless otherwise indicated:

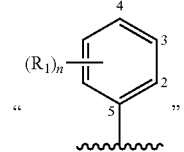

The term "symmetric" means that the 2 units present in the compounds of formula (I) or (II), are strictly identical (even $R_1$, even n, and even positions on the ring).

The term "anion or anionic counterion" means an anion or a cosmetically acceptable inorganic or organic anionic group derived from an organic or mineral acid salt associated with the cationic charge of the dye; more particularly, the anion is chosen from: i) halides such as chloride or bromide; ii) allvisulfonates, including $C_1$-$C_6$ alkyisulfonates: Alk-S(O)$_2$O— such as methylsulfonate or mesylate and ethylsulfonate; iii) arylsulfonates: Ar—S(O)$_2$O$^-$ such as benzenesulfonate and toluenesulfonate or tosylate; iv) citrate; v) succinate; vi) tartrate; vii) lactate; viii) alkyl sulfates: Alk—O—S(O)O$^-$ such as methyl sulfate and ethyl sulfate; ix) aryl sulfates: Ar—O—S(O)O$^-$ such as benzene sulfate and toluene sulfate; x) alkoxy sulfates: Alk—O—S(O)$_2$O$^-$ such as methoxy sulfate and ethoxy sulfate; xi) aryloxy sulfates: Ar—O—S(O)$_2$O$^-$, xii) phosphates O=P(OH)$_2$—O$^-$, O=P(O$^-$)$_2$—OH 0=P(O$^-$)$_3$, HO—[P(O)(O$^-$)]$_w$—P(O)(O$^-$)$_2$ with w being an integer; xiii) acetate; xiv) triflate; xv) borates such as tetrafluoroborate, xvi) disulfate S(O)$_2$O$_2^-$; xvii) carbonate; and xviii) hydrogen carbonate;

more particularly, the cosmetically acceptable anions are chosen in particular from halides such as chloride, methosulfates, alkylsulfonates: Alk—S(O)$_2$O$^-$ such as methylsulfonate or mesylate and ethylsulfonate; arylsulfonates: Ar—S(O)$_2$O$^-$ such as benzenesulfonate and toluenesulfonate or tosylate; citrate; succinate; tartrate; lactate; alkyl sulfates: Alk—O—S(O)O$^-$ such as methyl sulfate; aryl sulfates such as benzene sulfate and toluene sulfate; phosphate; acetate; triflate; borates such as tetrafluoroborate; carbonate; and hydrogen carbonate.

As the anion, derived from the organic or mineral acid salt, ensures the electrical neutrality of the molecule, it is understood that when the anion comprises several anionic charges, then the same anion may serve for the electrical neutrality of several cationic groups in the same molecule or else may serve for the electrical neutrality of several molecules; for example, a dye of formula (I) or (II) which contains two cationic groups may contain either two "singly charged" anionic counterions or one "doubly charged" anionic counterion such as $S(O)_2O_2^-$ or $O=P(O^-)_2$—OH; and when the compounds of formulae (I) and (II) bear one or more sulfonate groups $SO_3^-$ $M^+$, it is understood that the compounds of formulae (I) and (II) can respect the electrical neutrality by comprising neither $M^+$ nor $An^-$, the sulfonate group(s) being "electro-compensated" by the presence of a corresponding amount of cationic charge via the cationic heterocycle(s) and/or ammonium radical(s);

By way of example:

when the groups R, of the compounds of formula (I) or (II) bear a cationic charge and when none of the substituents bears an $SO_3^-$ or $CO_2^-$ radical, then the compounds of formula (I) or (II) comprise two singly charged anions $An^-$ such as two chloride anions or a doubly charged anion such as a sulfate, such that the corresponding compound of formula (I) or (II) is globally neutral (electrical neutrality);

when the groups R, of the compounds of formula (I) or (II) bear a cationic charge and when two substituents bear an $SO_3^-$ or $CO_2^-$ radical, then the compounds of formula (I) or (II) do not comprise any anions $An^-$ such that the corresponding compound of formula (I) or (H) is globally neutral.

The term "cation or cationic counterion" means a cosmetically acceptable organic or inorganic cation or cationic group derived from an organic or mineral base salt associated with the anionic charge of the dye; more particularly, the cationic counterion is chosen from i) alkali metals such as $Na^+$ and $K^+$, ii) alkaline-earth metals such as $Ca^{++}$ and $Mg^{++}$, and iii) ammoniums such as $R_aR_bR_cR_dN^+$ with $R_a$, $R_b$, $R_c$, and $R_d$, which may be identical or different, representing a hydrogen atom or a hydroxyl or $(C_1-C_8)$alkyl group.

The term "alkyl" means a saturated, linear or branched, preferably $C_1-C_6$ hydrocarbon-based radical;

The term "hydroxyalkyr" means an alkyl group as defined previously substituted with one or more hydroxyl groups, preferably a $(C_1-C_6)$alkyl group substituted with a hydroxyl group, such as hydroxyethyl;

The term "(hydroxy)alkyl" means an alkyl or hydroxyalkyl group as defined previously;

The term "alkoxy" means an —O-alkyl group with alkyl as defined previously: in particular, alkoxy denotes a methoxy or ethoxy group;

The term "cationic heterocycle" means a monocyclic or bicyclic, preferably monocyclic, 5- to 10-membered, preferably 5- to 8-membered heterocycle, at least one member of which is a heteroatom bearing a cationic charge such as N', said heterocycle being saturated or unsaturated, aromatic or non-aromatic, and also possibly comprising at least one heteroatom, chosen from oxygen, nitrogen and/or sulfur atoms;

The aromatic cationic heterocycles (also known as cationic heteroaryls) are preferably chosen from imidazoliums, pyridiniums, pyrimidiniums, benzimidazoliums, benzothiazoliums, oxazoliums, benzotriazoliums, pyrazoliums, thiazoliums, triazoliums and benzoxazoliums;

The non-aromatic cationic heterocycles are in particular saturated cationic heterocycles, and are preferably chosen from piperaziniums, pyrrolidiniums, morpholiniums and piperidiniums; each of said aromatic or non-aromatic, 5- to 10-membered cationic heterocycles possibly being substituted with one or more identical or different radicals chosen from (hydroxy)$(C_1-C_4)$alkyl radicals;

The term "non-cationic heterocycle" means an aromatic or non-aromatic, 5- to 10-membered, preferably 5- to 6-membered, uncharged heterocycle, containing at least one heteroatom chosen from oxygen, nitrogen and/or sulfur atoms, preferably containing at least one nitrogen atom, and optionally substituted with:

a 5- to 10-membered cationic heterocycle as described above, preferably chosen from i) imidazolium, ii) pyridinium, iii) piperazinium, iv) pyrrolidinium, v) morpholinium, vi) pyrimidinium, vii) thiazolium, viii) benzimidazolium, ix) benzothiazolium, x) oxazolium, benzotriazolium, xi) pyrazolium, xii) triazolium, xiii) benzoxazolium, xiv) piperidinium; said cationic heterocycle being optionally substituted with one or more radicals, which may be identical or different, chosen from (hydroxy)$(C_1-C_4)$aikyl radicals; and/or a $C_1-C_4$ tri(hydroxy)alkylammonium radical, for instance trimethylammonium, triethylammonium, dimethylethylammonium, diethylmethylammonium, diisopropylmethylammonium, diethylpropylammonium, 2-hydroxyethyldiethylammonium, p-dihydroxyethylmethylammonium, $1^{3-}$ trihydroxyethylammonium, dimethyihydroxyethylammonium, β-hydroxyethyldimethylammonium or β-hydroxyethylmethylethylammoniurn.

the "aryr" or "heteroaryr" or "heterocyclic" radicals may be substituted with at least one substituent borne by a carbon atom, chosen from:

a $C_1-C_6$ alkyl radical optionally substituted with one or more radicals chosen from the following radicals: hydroxyl, C alkoxy, $C_2-C_4$ (poly)hydroxyalkoxy, acylamino, amino substituted with two identical or different $C_1-C_4$ alkyl radicals optionally bearing at least one hydroxyl group or the two radicals possibly forming, with the nitrogen atom to which they are attached, a saturated or unsaturated, optionally substituted, 5- to 7-membered and preferably 5- or 6-membered heterocycle optionally comprising another nitrogen or non-nitrogen heteroatom;

a halogen atom;

a hydroxyl group;

a $C_1-C_2$ alkoxy radical;

a $C_2-C_4$ (poly)hydroxyalkoxy radical;

an amino radical;

an amino radical substituted with one or two identicator different $C_1-C_6$ alkyl radicals, optionally bearing at least:

i) a hydroxyl group, ii) one amino group optionally substituted with one or two optionally substituted $C_1-C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
iii) a quaternary ammonium group —N$^+$R'R"R''', An$^-$ for which R', R" and R''', which may be identical or different, represent a hydrogen atom or a $C_1$-$C_4$ alkyl group and An$^-$ is as defined previously;
iv) or an optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the radical R is a hydrogen atom or a $C_1$-$C_4$ alkyl radical optionally bearing at least one hydroxyl group and the radical R' is a $C_1$-$C_2$ alkyl radical;

a carbamoyl radical ((R)$_2$N—C(O)—) in which the radicals R, which may be identical or different, represent a hydrogen atom or a $C_1$-$C_4$ alkyl radical optionally bearing at least one hydroxyl group;

an alkylsulfonylamino radical (R'—S(O)$_2$—N(R)—) in which the radical R represents a hydrogen atom or a $C_1$-$C_4$ alkyl radical optionally bearing at least one hydroxyl group and the radical R represents a $C_1$-$C_4$ alkyl radical or a phenyl radical; an aminosulfonyl radical ((R)$_2$N—S(O)$_2$—) in which the radicals R, which may be identical or different, represent a hydrogen atom or a $C_1$-$C_4$ alkyl radical optionally bearing at least one hydroxyl group;

a carboxylic radical in acid or salified (preferably with an alkali metal or a substituted or unsubstituted ammonium) form;

a cyano group;

a nitro or nitroso group;

a polyhaloalkyl group, preferentially trifluoromethyl;

the cyclic or heterocyclic part of a non-aromatic radical may be substituted with at least one substituent chosen from the following groups:
hydroxyl;
$C_1$-$C_4$ alkoxy or $C_2$-$C_4$ (poly)hydroxyalkoxy;
$C_1$-$C_4$ alkyl;
alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;
alkylcarbonyloxy (R—C(O)—O—) in which the radical R is a $C_1$-$C_4$ alkyl radical or an amino group optionally substituted with one or two identical or different $C_1$-$C_4$ alkyl groups optionally bearing at least one hydroxyl group, said alkyl radicals possibly forming with the nitrogen atom to which it is attached a saturated or unsaturated, optionally substituted 5- to 7-membered heterocycle, optionally comprising at least one other nitrogen or non-nitrogen heteroatom;
alkoxycarbonyl (R-G-C(O)—) in which the radical R is a $C_1$-$C_4$ alkoxy radical, G is an oxygen atom or an amino group optionally substituted with a $C_1$-$C_4$ alkyl group optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;
a quaternary ammonium group —N$^+$R'R"R''', An$^-$ for which R', R" and R''', which may be identical or different, represent a hydrogen atom or a $C_1$-$C_4$ (hydroxy)alkyl group and An$^-$ is as defined previously;
a cyclic or heterocyclic radical, or a non-aromatic part of an aryl or heteroaryl radical, may also be substituted with one or more oxo groups.

1. Dyeing Process

The present invention also relates to a process for dyeing keratin fibres, in particular human keratin fibres such as the hair, in several steps, which comprises, in a first step, the application to said keratin fibres a) of a composition comprising one or more compounds of formula (I) and/or ill), particularly one or more compounds of formula (II), and then, in a second step, b) of an oxidizing composition, which comprises one or more chemical oxidizing agents, in particular chosen from hydrogen peroxide, urea peroxide, alkali metal bromates, persalts such as perborates and persuifates, peracids and oxidase enzymes (with the optional cofactors thereof), among which mention may be made of peroxidases, 2-electron oxidoreductases such as uricases, and 4-electron oxygenases such as laccases; preferably, the chemical oxidizing agent is hydrogen peroxide; it being understood that, between step a) and step b), said fibres may be rinsed, and/or washed and then optionally dried.

Preferably, said cosmetic composition is applied for a leave-on time of between 1 and 60 minutes, preferably between 5 and 40 minutes and even more preferentially between 10 and 30 minutes.

The cosmetic composition is generally applied to the keratin fibres at room temperature, preferably between 25 and 55° C.

According to one embodiment, the cosmetic composition according to the invention is applied to keratin fibres, especially human keratin fibres such as the hair, in the presence of one or more chemical oxidizing agents as described above, for a time that is sufficient to obtain the desired lightening.

The present invention also relates to a process for dyeing keratin fibres, in particular human keratin fibres such as the hair, in one or more steps, comprising the application to said keratin fibres of a composition which comprises the compound(s) of formula (I) and/or (II), particularly the compound(s) of formula (II), and optionally one or more chemical oxidizing agents, as defined previously, it being understood that after application of said composition which comprises the compound(s) of formula (l) and/or (II), said fibres may be rinsed, and/or washed and then optionally dried.

According to a particular embodiment, the dyeing process according to the invention uses one or more chemical oxidizing agents, as described above, separately from the cosmetic composition comprising one or more compounds of formula (I) and/or (II) in another cosmetic composition. The two cosmetic compositions may be mixed just before use or may be used separately.

According to one variant, the dyeing process according to the invention consists in applying to keratin fibres, especially human keratin fibres such as the hair, a ready-to-use cosmetic composition which results from the mixing of a cosmetic composition comprising one or more compounds of abovementioned formula (I) and/or (II) and an oxidizing cosmetic composition comprising one or more chemical oxidizing agents, as described previously. The ready-to-use cosmetic composition that is thus applied to the keratin fibres may be in various forms, such as in the form of liquids, creams or gels, or in any other form that is suitable for dyeing keratin fibres, and in particular human hair.

According to another variant, the dyeing process according to the invention consists in applying to the keratin fibres, in particular human keratin fibres such as the hair, (i) the cosmetic composition comprising, in a suitable dyeing medium, one or more compounds of formula (I) and/or (II) as defined previously, free of chemical oxidizing agent, and (ii) a cosmetic composition comprising one or more chemical oxidizing agents as defined previously; compositions (i) and (ii) being applied to said keratin fibres sequentially or simultaneously for a time that is sufficient to obtain the desired lightening, and the fibres are then rinsed, optionally washed with shampoo, rinsed again, and the resulting fibres are dried or left to dry.

The oxidizing composition may also contain various adjuvants conventionally used in cosmetic compositions, in particular compositions for dyeing the hair and as defined previously.

For the purposes of the present invention, the term "sequentially" means that the oxidizing composition is applied before or after the cosmetic composition, i.e. as a pre-treatment or a post-treatment, preferably as a pre-treatment.

The pH of the oxidizing composition containing the chemical oxidizing agent is such that, after mixing with the cosmetic composition, the pH of the resulting composition applied to the keratin fibres preferably ranges between 2 and 12 approximately, even more preferentially between 3 and 10 and even more particularly between 4 and 9.5. It may be adjusted to the desired value by means of acidifying or basifying agents usually used in the dyeing of keratin fibres.

Among the acidifying agents that may be mentioned, by way of example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkaline carbonates, alkanolamines such as monoethanolamine, diethanolamine and triethanolamine, and also derivatives thereof, sodium hydroxide, potassium hydroxide and the compounds of formula (III) below: $R_aR_bN-Z-NR_cR_d$: in which Z is a linear or branched $(C_1-C_6)$alkylene group, which is optionally substituted, especially with one or more hydroxyl or amino groups, and preferably Z=propylene optionally substituted with a hydroxyl group or a $C_1-C_4$ alkyl radical; $R_a$, $R_b$, $R_c$ and $R_d$, which may be identical or different, represent a hydrogen atom or a $C_1-C_4$ alkyl or $C_1-C_4$ hydroxyalkyl radical.

Preferably, the azomethine direct dyes of formula (I) and the precursors of direct dyes of formula (II) used according to the process of the invention are such that, taken together or separately.

$R_1$ represents:
  a sulfonic radical —$SO_3H$ or sulfonate radical —$SO_3$;
  a hydrogen atom;
  a radical —W'—$R'_7$, in which:
    W' represents an oxygen or sulfur atom or a divalent group —$N(R'_8)$—;
    $R'_7$ and $R'_8$, which may be identical or different, represent a linear or branched, saturated or unsaturated, preferably saturated, alkyl group, comprising from 1 to 8 carbon atoms, said hydrocarbon-based chain being:
      optionally substituted with one or more radicals, which may be identical or different, chosen from the following radicals: i) hydroxyl, ii) (di)($C_1-C_6$) (alkyl)amino, iii) ammoniums —$N^+RR'R''$ with R, R' and R'' as defined previously, iv) aromatic or non-aromatic, optionally substituted, 5- to 10-membered cationic heterocycles, preferably a 5- or 6-membered cationic heteroaryl optionally substituted with one or more ($C_1-C_4$)alkyl groups, such as ($C_1-C_4$)(alkyl)imadazoliums, ($C_1-C_4$)(alkyl)piperaziniums, $C_1-C_4$)(alkyl)pyrrolidiniums, ($C_1-C_4$)(alkyl)piperidiniums, morpholiniums, v) aromatic or non-aromatic, 5- or 6-membered non-cationic heterocycles, substituted with a radical chosen from the following radicals: a) ammonium —$N^+RR'R''$, $An^-$ with R, R' and R'' as defined previously, and b), aromatic, 5- to 10-membered cationic heterocycle, optionally substituted with one or more radicals, which may be identical or different, chosen from $C_1-C_4$ alkyl; preferably, the cationic heterocycle is a ($C_1-C_4$)(alkyl)imidazolium: and/or
    optionally interrupted with one or more divalent heteroatoms or groups, which may be identical or different, chosen from:
    —O—, —$N(R_{10})$—, and —C(O)—, with $R_{10}$ as defined previously, and
    combinations thereof:
      preferably starting and/or terminating and/or optionally interrupted with:
        —$N(R_{10})$—, —O—C(O)—, —C(O)—O—, —C(O)—N(H)—, —N(H)—C(O)—, —N(H)—C(O)—N(H)—, —O—C(O)—N(H)—, —N(H)—C(O)—O—, or —N(H)—C(NH)—NH—;
  $R'_7$ and $R'_8$, which may be identical or different, represent:
    a hydrogen atom,
    a linear or branched $C_1-C_{14}$, in particular $C_1-C_8$ and preferably $C_1-C_6$ alkyl group, said alkyl group being:
      optionally interrupted with one or more heteroatoms or groups, which may be identical or different, such as —O—, —S—, —$N(R_{10})$—, —S(O)—, —$S(O)_2$— and —C(X)— with X and $R_{10}$ as defined previously, or combinations thereof; and/or
      optionally substituted with one or more radicals, which may be identical or different, chosen from the following radicals: i) hydroxyl, ii) (di)($C_1-C_6$)(alkyl)amino, iii) ammoniums —$N^+RR'R''$ with R, R' and R'' as defined previously, iv) aromatic or non-aromatic, optionally substituted, 5- to 10-membered cationic heterocycles, preferably a 5- or 6-membered cationic heteroaryl optionally substituted with one or more ($C_1-C_4$)alkyl groups, such as ($C_1-C_4$)(alkyl)imidazolium, v) aromatic or non-aromatic, 5- or 6-membered non-cationic heterocycles, substituted with a radical a) ammonium —$N^{30}$ RR'R'' with R, R' and R'' as defined previously, and b), aromatic or non-aromatic, 5- to 10-membered cationic heterocycle, optionally substituted especially with one or more identical or different radicals chosen from $C_1$-$C_4$ alkyl; preferably, the cationic heterocycle is a cationic heteroaryl optionally substituted with one or more ($C_1$-$C_4$)alkyl groups, such as ($C_1$-$C_4$)(alkyl)imidazolium;

n represents an integer equal to 0 or 1;

$R_3$ and $R_4$, which may be identical or different, represent a hydrogen atom, a ($C_1$-$C_6$)alkyl radical, or a ($C_1$-$C_6$)alkyl radical substituted with one or more radicals chosen from hydroxyl and/or $C_1$-$C_4$ alkoxy; preferentially $R_3$ and $R_4$ represent a hydrogen atom;

$R_5$ and $R_6$ represent a hydrogen atom;

$An^-$ is an anionic counterion as defined previously, preferably chosen from bromide, chloride, methyl sulfate and toluenesulfonate ions or a mixture of these ions; more preferentially, $An^-$ is a halide and even more preferentially a chloride.

According to a particular embodiment of the invention, the azomethine direct dye(s) of formula (I) and the precursors of direct dyes of formula (II) used according to the process of the invention are such that $R_1$ represents:

a radical —$OR_7$;
a radical —$SR_7$;
a radical —$NR_7R_8$;
a linear or branched $C_1$-$C_{14}$, in particular $C_1$-$C_8$ and preferably $C_1$-$C_6$ alkyl radical, said alkyl radical being:
  optionally interrupted with one or more heteroatoms or groups, which may be identical or different, chosen from —O—, —S—, —N(H)—, —N($R_{10}$)— with Rio as defined previously, —S(O)—, S(O)$_2$, and —C(X)— with X representing an oxygen or sulfur atom or N—R with R as defined previously, or combinations thereof preferably chosen from: —O—C(O)—. —C(O)—O—, —C(O)—N(H)—, —N(H)—C(O)—, —N(H)—C(O)—N(H)—, —O—C(O)—N(H)—, —N(H)—C(O)—O—, —N(H)—C(NH)—NH—; and/or
  optionally substituted with one or more radicals, which may be identical or different, chosen from the following radicals: i) hydroxyl, ii) $C_5$-$C_4$ alkoxy, iii) amino —$NH_2$, iv) $C_1$-$C_6$ mono- and/or dialkylamino, v) ammoniums —$N^+RR'R''$ with R, R' and R'' as defined previously, and vi) optionally substituted, aromatic or non-aromatic, 5- to 10-membered cationic heterocycles, preferably a 5- or 6-membered cationic heteroaryl optionally substituted with one or more ($C_1$-$C_4$)alkyl groups, such as ($C_1$-$C_4$)(alkyl)imidazalium, vii) aromatic or non-aromatic, 5- or 6-membered non-cationic heterocycles, substituted with a radical chosen from the following radicals:
  ammoniums —with R, R' and R'' as defined previously, and/or
  optionally substituted, aromatic or non-aromatic, 5- to 10-membered cationic heterocycle, preferably a cationic heteroaryl optionally substituted with one or more ($C_1$-$C_4$)alkyl groups, such as ($C_1$-$C_4$)(alkyl)imidazolium;
  a hydroxyl, amino, $C_1$-$C_4$ alkylamino, dialkylamino, alkoxy, $C_1$-$C_4$ alkyl or $C_1$-$C_4$ hydroxyalkyl radical, a linear or branched $C_1$-$C_{14}$, in particular $C_1$-$C_8$ and preferably $C_1$-$C_6$ alkoxy radical, said alkoxy radical being:
optionally interrupted with one or more heteroatoms or groups, which may be identical or different, chosen from —O—, —S—, —N($R_{10}$)— with $R_{10}$ as defined previously, —S(O)—, S(O)$_2$, and —C(X)— with X representing an oxygen or sulfur atom or N—R with R as defined previously, or combinations thereof preferably chosen from: —O—C(O)—, —C(O)—O—, —C(O)—N(H)—, —N(H)—C(O)—, —N(H)—C(O)—N(H)—, —O—C(O)—N(H)—. —N(H)—C(O)—O—, —N(H)—C(NH)—NH—; and/or optionally substituted with one or more radicals, which may be identical or different, chosen from the following radicals: i) hydroxyl, ii) $C_1$-$C_4$ alkoxy, iii) amino —$NH_2$, iv) $C_1$-$C_6$ mono- and/or dialkylamino, v) ammoniums —$N^+RR'R''$ with R, R' and R'' as defined previously, and vi) optionally substituted, aromatic or non-aromatic, 5- to 10-membered cationic heterocycles, preferably a 5- or 6-membered cationic heteroaryl optionally substituted with one or more ($C_1$-$C_4$)alkyl groups, such as ($C_1$-$C_4$)(alkyl)imidazolium, vii) aromatic or non-aromatic, 5- or 6-membered non-cationic heterocycles, substituted with a radical chosen from the following radicals:
ammoniums —$N^+RR'R''$ with R, R' and R'' as defined previously, and/or
optionally substituted, aromatic or non-aromatic, 5- to 10-membered cationic heterocycle, preferably a cationic heteroaryl optionally substituted with one or more ($C_1$-$C_4$)alkyl groups, such as ($C_1$-$C_4$)(alkyl)imidazolium;
a hydroxyl, amino, $C_1$-$C_4$ alkylamino, dialkylamino, alkoxy, $C_1$-$C_4$ alkyl or $C_1$-$C_4$ hydroxyalkyl radical.

According to a particular embodiment of the invention, the azomethine direct dye(s) of formula (I) and the precursors of direct dyes of formula (II) used according to the process of the invention are such that $R_1$ represents a group —W—$R_7$, in which W represents an oxygen atom or a divalent group —N($R_8$)—, with $R_7$ and $R_8$, which may be identical or different, represent:
a hydrogen atom,
a ($C_1$-$C_8$)alkyl group:
  optionally interrupted with one or more heteroatoms or groups, which may be identical or different, chosen from —O—, —S—, —N($R_{10}$)— with R as defined previously, —S(O)—, S(O)$_2$, and —C(X)— with X representing an oxygen or sulfur atom or N—$R_{10}$ with $R_{10}$ as defined previously, or combinations thereof preferably chosen from: —O—C(O)—, —C(O)—O—, —C(O)—N(H)—, —N(H)—C(O)—, —N(H)—C(O)—N(H)—, —O—C(O)—N(H)—, —N(H)—C(O)—O—, —N(H)—C(NH)—NH—; and/or
  optionally substituted with one or more radicals, which may be identical or different, chosen from:
  hydroxyl radicals;
  a optionally substituted, aromatic or non-aromatic, 5- to 10-membered cationic heterocycles, preferably an aromatic or non-aromatic, 5- or 6-membered cationic heterocycle, optionally substituted with one or more $(C_1-C_4)$alkyl groups, such as imidazoliums, piperaziniums, pyrrolidiniums, morpholiniums and piperidiniums, ammoniums —$N^+RR'R''$ with R, R' and R'' as defined previously, a aromatic or non-aromatic, 5- or 6-membered non-cationic heterocycles, substituted with a radical chosen from ammonium radicals —$N^+RR'R''$ with R, R' and R'' as defined previously, and/or with an optionally substituted, aromatic or non-aromatic, 5- to 10-membered cationic heterocycle, preferably a cationic heterocycle optionally substituted with one or more $(C_1-C_4)$alkyl groups, such as an imidazolium, a piperazinium, a pyrrolidinium, a morpholinium and a piperidinium.

According to another particularly advantageous embodiment, the azomethine direct dyes of formula (I) and the precursors of direct dyes of formula (A) used according to the process of the invention are such that n represents an integer equal to 1, and $R_1$ is in position 4.

Preferably, the ammonium radicals —$N^{30}RR'R''$ described above are chosen from trimethylammonium, triethylammonium, dimethylethylammonium, diethylmethylammonium, diisopropylmethylammonium, diethylpropylammonium, 2-hydroxyethyldiethylammonium, β-dihydroxyethylmethylammonium, β-trihydroxyethylammonium, dimethylhydroxyethylammonium, 2-hydroxyethyldimethylamnrionium and 2-hydroxyethylmethylethylammonium; preferentially, the ammonium radicals —$N^+RR'R''$ are chosen from trimethylammonium and 2-hydroxyethylmethylethylammonium.

According to a particular embodiment of the invention, the cationic heterocycles are 5- to 10-membered and aromatic; preferably chosen from imidazoliums, pyridiniums, pyrimidiniums, benzimidazoliums, benzothiazoiiums, oxazoliums, benzotriazoliums, pyrazoliums, thiazoliums, triazoliums and benzoxazoliums; optionally substituted with one or more radicals, which may be identical or different, chosen from (hydroxy)$(C_1-C_4)$alkyl radicals.

According to another embodiment of the invention, the cationic heterocycles are 5- to 10-membered and non-aromatic; preferably chosen from piperaziniums, pyrrolidiniums, morpholiniums, thiazoliums and piperidiniums; each of said non-aromatic 5- to 10-membered cationic heterocycles possibly being substituted with one or more radicals, which may be identical or different, chosen from (hydroxy)$(C_1-C_4)$alkyl radicals.

According to an advantageous variant of the invention, the cationic heterocycles are imidazoliums, which are optionally substituted, especially with one or more identical or different radicals chosen from (hydroxy)$(C_1-C_4)$alkyl radicals, such as a methyl.

According to another preferential embodiment of the invention, the cationic heterocycles are chosen from imidazoliums, piperaziniums, pyrrolidiniums, morpholiniums and piperidiniums; optionally substituted with one or more radicals, which may be identical or different, chosen from (hydroxy)$(C_1-C_4)$alkyl radicals.

According to a particular embodiment of the invention, the non-cationic heterocycles are 5- or 6-membered; preferably chosen from piperidines, piperazines, pyrrolidines, morpholines, thiazoles, imidazoles and pyridines, more preferentially chosen from piperidines, piperazines, pyrrolidines, morpholines and imidazoles, the 5- or 6-membered non-cationic heterocycles possibly being substituted especially with:

an ammonium radical —$N^+RR'R''$ with R, R' and R'', which may be identical or different, representing a $(C_1-C_4)$alkyl group optionally substituted with one or more hydroxyl groups, such as methyl, ethyl, propyl or 2-hydroxyethyl, and/or an aromatic or non-aromatic, 5- to 10-membered cationic heterocycle, which is optionally substituted, especially with one or more identical or different radicals chosen from (hydroxy)$(C_1-C_4)$alkyl radicals.

According to a particular embodiment of the invention, the non-cationic heterocycles are 5- or 6-membered and non-aromatic, preferably chosen from piperazines, pyrrolidines, morpholines and piperazines, and more preferentially pyrrolidines; said 5- or 6-membered non-cationic heterocycles possibly being substituted especially with:

an ammonium radical —$N^+RR'R''$ with R, R' and R'', which may be identical or different, representing a $(C_1-C_4)$alkyl group optionally substituted with one or more hydroxyl groups, such as methyl, ethyl, propyl or 2-hydroxyethyl, and/or an aromatic or non-aromatic. 5- to 10-membered cationic heterocycle, which is optionally substituted, especially with one or more identical or different radicals chosen from (hydroxy)$(C_1-C_4)$alkyl radicals.

According to another embodiment of the invention, the non-cationic heterocycles are 5- or 6-membered and aromatic, preferably chosen from imidazoles, pyridines, pyrimidines, benzimidazoles, benzothiazoles, oxazoles, benzotriazoles, pyrazoles, thiazoles, triazoles and benzoxazoles; said 5- or 6-membered non-cationic heterocycles possibly being substituted especially with:

an ammonium radical —$N^+RR'R''$ with R, R' and R'', which may be identical or different, representing a $(C_1-C_4)$alkyl group optionally substituted with one or more hydroxyl groups, such as methyl, ethyl, propyl or 2-hydroxyethyl, and/or an aromatic or non-aromatic, 5- to 10-membered cationic heterocycle, which is optionally substituted, especially with one or more identical or different radicals chosen from (hydroxy)$(C_1-C_4)$alkyl radicals.

According to a particular embodiment of the invention, the non-cationic heterocycles contain at least one heteroatom chosen from O and N, and are substituted with one or more identical or different $C_1-C_4$ tri(hydroxy)alkylammonium radicals chosen from trimethylammonium, triethylammonium, dimethylethylammonium, diethylmethylammonium, diisopropylmethylammonium, diethylpropylammonium, 2-hydroxyethyldiethylammonium, p-dihydroxyethylmethylethylammanium, β-trihydroxyethylammonium, dimethylhydroxyethylammonium, β-hydroxyethyldimethylammonium and 2-hydroxyethylmethylethylammonium; preferentially, the non-cationic heterocycles contain at least one heteroatom chosen from O and N, and are substituted with one or more identical or different $C_1-C_4$ tri(hydroxy)alkylammonium radicals chosen from trimethylammonium and 2-hydroxyethylmethylethylammonium.

According to an advantageous variant of the invention, the non-cationic heterocycles are pyrrolidines substituted especially with:

one or more identical or different ammonium radicals $N^4RR'R''$ with R. R' and R'' as defined previously, preferably a trimethylammonium radical, and/or an aromatic or non-aromatic, 5- to 10-membered cationic heterocycle, which is optionally substituted with one or more (hydroxy)($C_1$-$C_4$)alkyl groups.

According to a particularly advantageous embodiment of the invention, $R_1$ represents a group chosen from:

hydroxyl, amino,

—$SO_3H$, (di)(hydroxy)($C_1$-$C_6$)alkylamino, (hydroxy)($C_1$-$C_6$)alkoxy, in particular $C_1$-$C_6$ alkoxy such as methoxy or ethoxy, (di)(alkoxy)alkylamino, Preferably, the process according to the invention is characterized in that the azomethine direct dyes of formula (I) and (II) are chosen from the following compounds and the geometrical or optical isomer forms thereof, the tautomers thereof, the organic or mineral acid or base salts thereof or the solvates thereof such as hydrates:

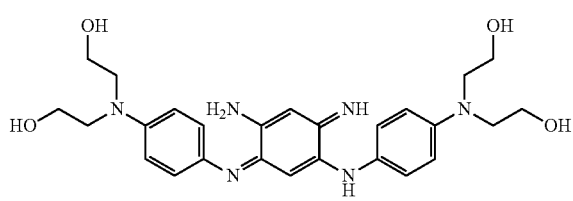

(1)

2-[{4-[2-Amino-5-{4-[bis(2-hydroxyethyl)amino]phenylamino}-4-iminocyclohexa-2,5-dienylideneamino]phenyl}(2-hydroxyethyl)amino]ethanol

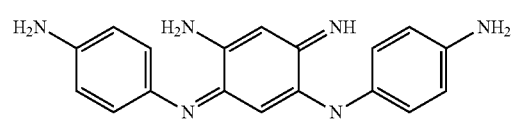

(2)

N-1-(4-Aminophenyl)-3-[(Z)-4-aminophenylimino]-6-iminocyclohexa-1,4-diene-1,4-diamine

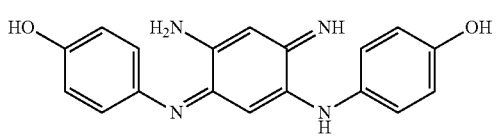

(3)

4-({2-Amino-5-[(4-hydroxyphenyl)amino]-4-iminocyclohexa-2,5-dien-1-ylidene}amino)phenol

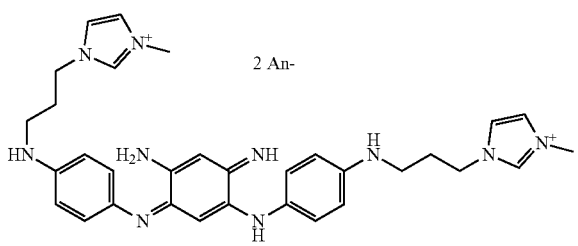

(4)

Salt of 1-(3-{[4-({2-amino-4-imino-5-[(4-{[3-(3-methyl-1H-imidazol-3-ium-1-yl)propyl]amino}phenyl)amino]cyclohexa-2,5-dien-1-ylidene}amino)phenyl]amino}propyl)-3-methyl-1H-imidazol-3-ium 2 An⁻

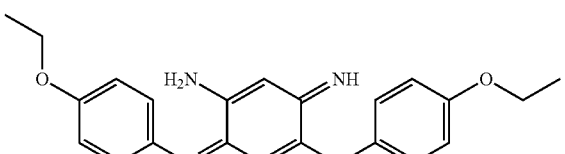

(5)

N-1-(4-Ethoxyphenyl)-3-[4-ethoxyphenylimino]-6-iminocyclohexa-1,4-diene-1,4-diamine

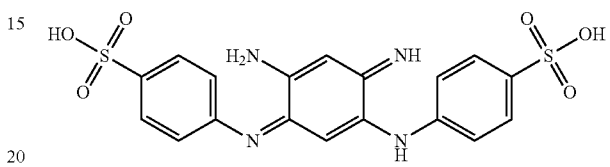

(6)

4-({2-Amino-4-imino-5-[(4-sulfophenyl)amino]cyclohexa-2,5-dien-1-ylidene}amino)benzenesulfonic acid

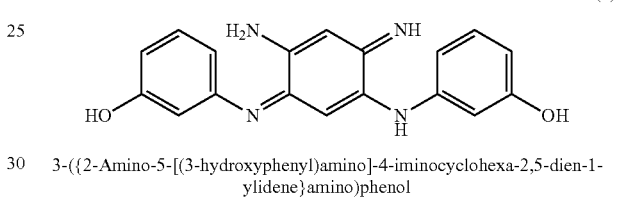

(7)

3-({2-Amino-5-[(3-hydroxyphenyl)amino]-4-iminocyclohexa-2,5-dien-1-ylidene}amino)phenol with An as defined previously.

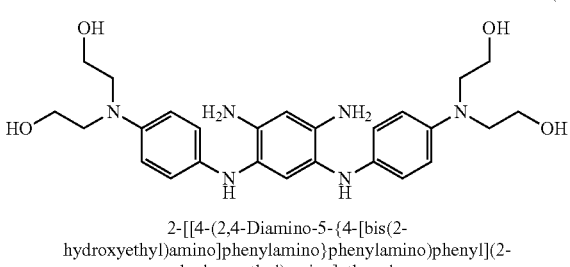

(1')

2-[[4-(2,4-Diamino-5-{4-[bis(2-hydroxyethyl)amino]phenylamino}phenylamino)phenyl](2-hydroxyethyl)amino]ethanol

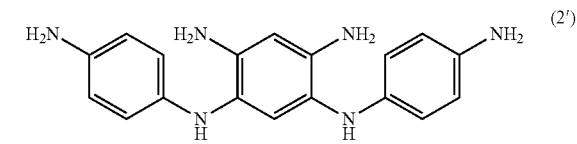

(2')

N,N'''-Bis(4-aminophenyl)benzene-1,2,4,5-tetramine

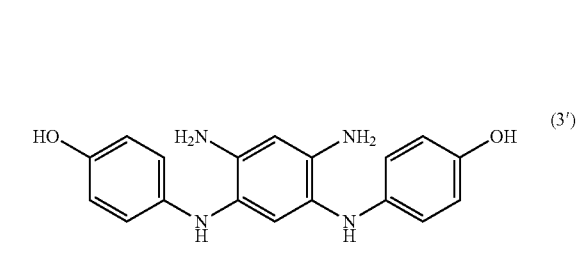

(3')

N,N'''-Bis(4-hydroxyphenyl)benzene-1,2,4,5-tetramine

-continued (4')

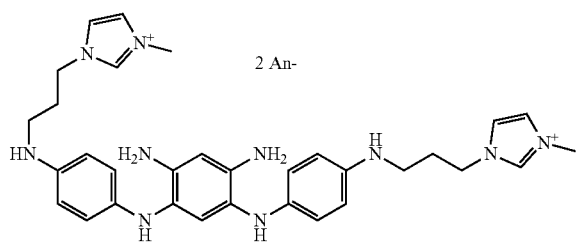

N,N'''-Bis(4{[3-(3-methyl-1H-imidazol-3-ium-1-yl)propyl]amino}phenyl)benzene-1,2,4,5-tetramine (5')

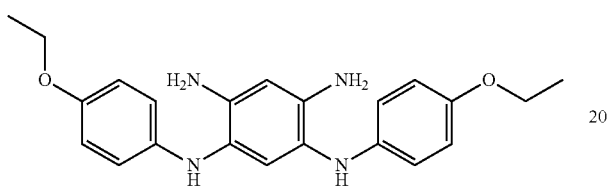

N,N'''-Bis(4-ethoxyphenyl)benzene-1,2,4,5-tetramine (6')

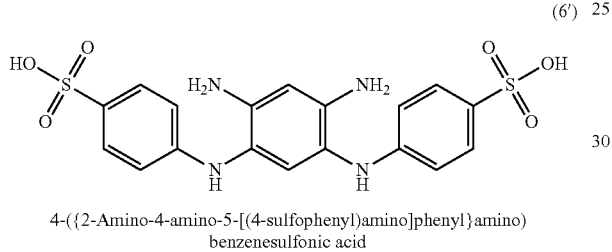

4-({2-Amino-4-amino-5-[(4-sulfophenyl)amino]phenyl}amino)benzenesulfonic acid (7')

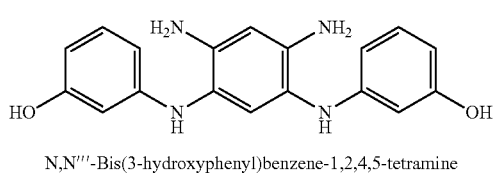

N,N'''-Bis(3-hydroxyphenyl)benzene-1,2,4,5-tetramine with An as defined previously.

Preferably, the direct dyes of formula (I) according to the process of the invention are of structure (1), (2), (3), (4), (5), (6), or (7) and also the geometrical or optical isomer forms thereof, the tautomers thereof, the organic or mineral acid or base salts thereof or the solvates thereof such as hydrates.

Preferably, the direct dyes of formula (II) according to the process of the invention are of structure (1'), (2'), (3'), (4'), (5'), (6'), or (7') and also the geometrical or optical isomer forms thereof, the tautomers thereof, the organic or mineral acid or base salts thereof or the solvates thereof such as hydrates.

According to the process of the invention, the compounds of formula (I) and (II) may optionally be salified with mineral acids, for instance HCl, HBr, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

According to the process of the invention, the compounds of formula (I) and (II) may also be in the form of solvates, for example a hydrate or a solvate of a linear or branched alcohol, for instance ethanol or isopropanol.

II. Azomethine Direct Dyes of Formula (I) and (II)

The present invention also relates to the novel compounds of formula (I), and of leuco type of formula (II) below, the organic or mineral, acid or base salts thereof, the tautomeric forms, optical isomers and geometrical isomers thereof, and/or the solvates thereof.

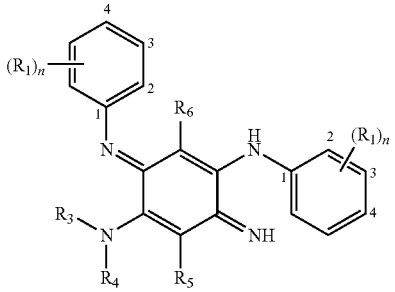

(I)

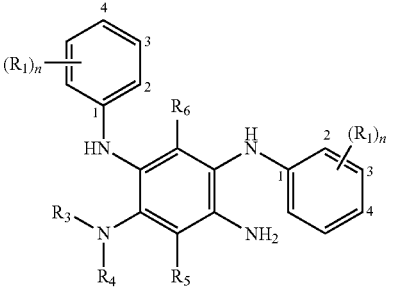

(II)

it being understood that the compound(s) of formula (I) are other than the compound:

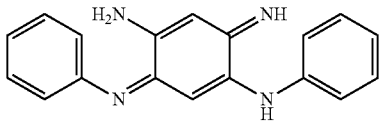 [SMILES: N=C1C=C(N)/C(=N\c2ccccc2)C=C1Nc1ccccc1]

described previously in Empson, J et al., Justus Liebigs Annalen der Chemie (1912), 389, pages 345-387.

In said formulae (I) and (II), $R_1$, $R_3$, $R_4$, $R_5$, $R_6$, $R_8$, $R_9$, $R_{10}$ have the same meanings and have the same preferences as those indicated previously in formula (I) or (II) of the compounds used in the process according to the invention, and it being understood that:

the compounds of formulae (I) and (II) are symmetrical,
when the compound of formulae (I) and (II) is cationic, it comprises one or more An⁻ to ensure the electrical neutrality of the molecule, and
when the compound of formulae (I) and (II) is cationic and comprises a sulfonate group, then M⁺ and An⁻ may be absent to ensure the electrical neutrality of said molecule. In particular, the preferred variants of n, $R_1$, $R_3$, $R_4$, $R_5$, $R_6$, $R_8$, $R_9$ and $R_{10}$ of the cationic heterocycles, of the non-cationic heterocycles and of the ammonium radicals in formula (I) and/or (II) of the compounds corresponding to those indicated in formula (I) and/or (II) of the compounds used in the process according to the invention.

Preferably, at least one of the substituents $R_1$, $R_3$, $R_4$, $R_5$ or $R_6$, of the compounds of formula (I) and/or (II), does not represent a hydrogen atom.

According to the invention, the compounds of formulae (I) and (II) may be optionally salified with mineral acids, for instance HCl, HBr, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

According to the invention, the compounds of formulae (I) and (II) may be optionally in the form of solvates, for example a hydrate or a solvate of a linear or branched alcohol, for instance ethanol or isopropanol.

Another subject of the invention is a process for preparing compounds of formula (I) and/or (II) as defined previously, according to the following schemes:

access to the compounds (I):

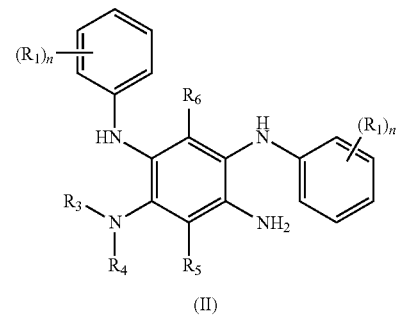

(II)

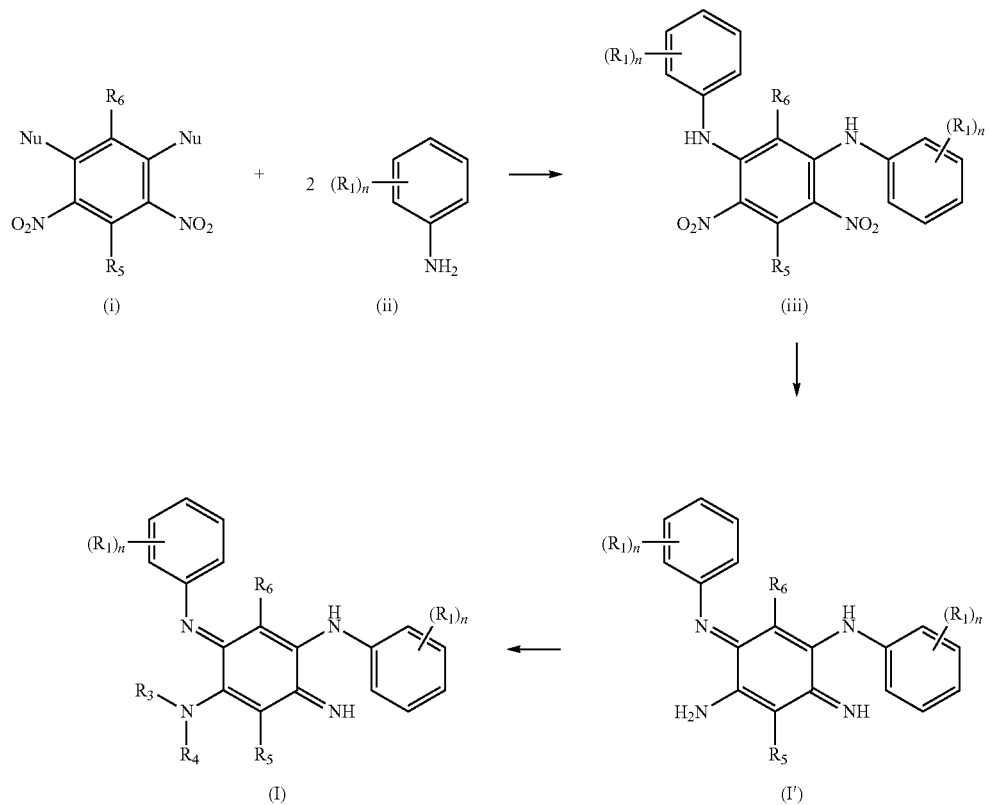

access to the compounds (II):

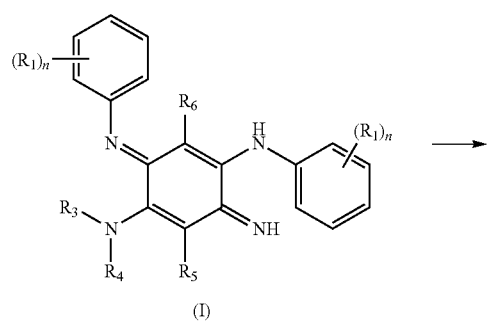

which consists for the compounds (I):

a) in a first stage, in reacting one molar equivalent of a 1,5-dinitrobenzene compound (i) comprising in positions 2 and 4 a nucleofugal group Nu with two molar equivalents of aniline compound (ii); Nu representing a nucleofugal group, such as a halogen atom, for instance a chlorine atom or a methoxide, tosylate, mesylate or sulfonate group. Preferably, this reaction is performed i) in a polar protic solvent such as in water or a mixture of water/$C_1$-$C_{10}$ alcohol such as ethanol or in a polar aprotic solvent such as in 1-methyl-2-pyrrolidinone, acetone, acetonitrile, pyridine or N,N-dimethylformamide, ii) and/or in the presence of one or more mineral or organic basifying agents, as defined below, chosen in particular from diisopropylethylamine, trimethylam ine, sodium hydroxide, potassium hydroxide, a mineral carbonate such as potassium carbonate, or an acetate, iii) and/or at a temperature of between 0° C. and 75° C., preferably at 75° C.; and then b) in a second stage, in maintaining the reaction medium under stirring for a time of between 5 minutes and 48 hours, more particularly between 30 minutes and 24 hours if the reaction is performed at room temperature; and then c) the reaction product (iii) is optionally purified via a standard technique such as recrystallization, filtration or chromatography;

d) according to another variant, compound (iii) is not purified;

e) in a third stage, in performing a reduction reaction on compound (iii). Preferably, the reduction of compound (iii) may be performed in the presence of hydrazine; of ammonium formate, or under a hydrogen atmosphere, and in the presence of a hydrogenation catalyst based especially on a metal, for example palladium, nickel or rhodium, the reduction preferentially being performed with palladium on charcoal (Pd/C) under a hydrogen atmosphere. Preferentially, this reaction is performed in a solvent such as esters, in particular such as $(C_1-C_6)$alkyl acetates, in particular ethyl acetate. $(C_1-C_6)$alkanols (i.e. a compound of formula R—OH with R=$(C_1-C_6)$-alkyl) such as ethanol or methanol, and mixtures thereof; better still, the solvent is ethanol, methanol or a mixture of the two; to give compound (I'), Compound (I') is a particular compound of formula (I) according to the invention, in which $R_3$ and $R_4$ represent a hydrogen atom.

The conditions under which the reduction may be performed, such as the temperature, the amount of metal, the hydrogen pressure, the reaction time and the concentration, may be determined by a person skilled in the art.

Advantageously, the reduction is performed at a temperature of between 20 and 25° C. in the presence of a catalytic amount of the hydrogenation catalyst, better still based on palladium such as Pd/C, and at a hydrogen pressure of greater than or equal to 1 bar, especially between 1 and 5 bar. The amount of catalyst is advantageously less than 10 mol % relative to the molar amount of the compound of formula (iii) to be hydrogenated;

f) compound (I') possibly being N-substituted with halogenated reagents $R_3$-Hal and $R_4$-Hal with Hal representing a halogen atom, preferably Cl or I, preferably with heating at the reflux point of the solvent and in the presence of an alkaline agent, in particular in a polar aprotic solvent such as THF, to give compound (I) according to the invention after filtration, removal of the precipitate and optionally purification by chromatography or recrystallization:
it being understood that in the formulae (i), (ii), (iii), (i) and (ii), the radicals $R_1$ to $R_{10}$, and n are as defined previously.

The conditions under which the reduction may be performed on (iii), such as the temperature, the amount of metal, the hydrogen pressure, the reaction time and the concentration, may be determined by a person skilled in the art.

Advantageously, the reduction is performed at a temperature of between 20 and 25° C. in the presence of a catalytic amount of the hydrogenation catalyst, advantageously based on palladium such as Pd/C, and at a hydrogen pressure of greater than or equal to 1 bar, especially between 1 and 5 bar. The amount of catalyst is advantageously less than 10 mol % relative to the molar amount of the compound of formula (iii) to be hydrogenated.

The compounds of formula (i) are commercial compounds that are well known to those skilled in the art, such as 1,3-dichloro-4,6-dinitrobenzene (#CAS=3698-83-7) sold by Sigma-Aldrich under the reference 513237.

According to a particular embodiment, the compounds of formula (1), in which n represents an integer equal to 1, and $R_1$ is in position 4 and represents a hydroxyl group (case where $R_1$=–$WR_7$ with $W_7$ an oxygen atom and $R_7$ a hydrogen atom) or a group —$N(R_8)$—$R_7$ (case where $R_1$=—W—$R_7$ with $W_7$ a group —$N(R_8)$—), may be prepared according to the following preparation process

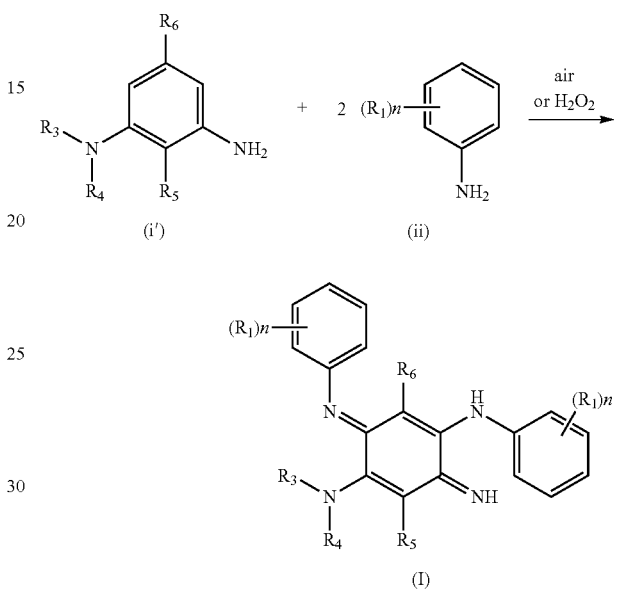

which consists:

a) in a first stage, in reacting, in the open air, one molar equivalent of 1,5-diaminobenzene compound (i') with two molar equivalents of aniline compound (ii). The pH of the solution is adjusted to an alkaline pH (pH above 7) with the aid of basifying agents as described previously, and optionally an excess of hydrogen peroxide is added to the solution. Preferably, this reaction is performed in a polar erotic solvent such as in water or a mixture of water/$C_1-C_{10}$ alcohol such as ethanol or in a polar aprotic solvent such as in 1-methyl-2-pyrrolidinone, acetone, acetonitrile, pyridine, N,N-dimethylformamide, ii) and/or in the presence of one or more mineral or organic basifying agents, as defined below, chosen in particular from diisopropylethylamine, triethylamine, sodium hydroxide, potassium hydroxide, a mineral carbonate such as potassium carbonate, or an acetate, iii) and/or at a temperature between 0° C. and 75° C., preferably at 25° C.; and then b) in a second stage, in keeping the reaction medium stirring for a time of between 5 minutes and 48 hours, more particularly between 30 minutes and 24 hours if the reaction is performed at room temperature; and then c) the compound of formula (1) is purified via a standard technique such as recrystallization, filtration or chromatography.

The compounds of leuco type corresponding to formula (II) are generally obtained by reacting the compounds of azomethine type of formula (I) with a reducing agent according to the reaction scheme below:

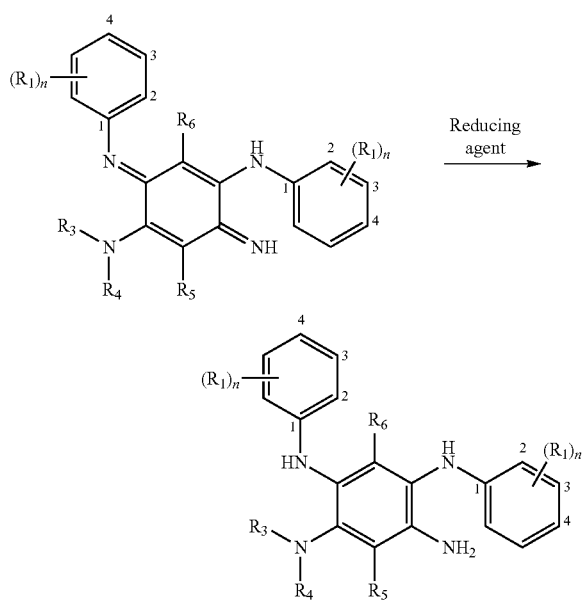

Synthetic approaches similar to this scheme are described in patent applications FR2056799, FR2047932, FR2165965 and FR2262023.

The compounds of leuco type of formula (II) are used as precursors for the direct dyes of formula (1), The characterization is performed by NMR spectroscopy and/or mass spectrometry.

III. Cosmetic Composition

The present invention also relates to a cosmetic composition, in particular for dyeing keratin fibres, more particularly human keratin fibres such as the hair, comprising one or more direct dyes of formula (I) and/or precursors of direct dyes (II) as defined previously and with the exception of the following compound:

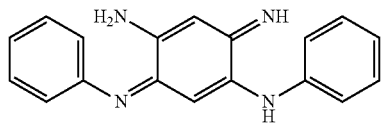 [SMILES: N=C1C=C(N)/C(=N\c2ccccc2)C=C1Nc1ccccc1]

Preferably, at least one of the substituents $R_1$, $R_3$, $R_4$, $R_5$, or $R_6$, of the compounds of formula (I) and/or (II), included in the cosmetic composition according to the invention, does not represent a hydrogen atom.

Preferably, the cosmetic composition comprises one or more azomethine direct dyes of formula (I) and/or (II) chosen from compounds (1) to (7) and compounds (1') to (7') as defined previously, the geometrical or optical isomer forms thereof, the tautomers thereof, the organic or mineral acid or base salts thereof or the solvates thereof such as hydrates, and also mixtures thereof.

According to a particular embodiment, the cosmetic composition comprises one or more azomethine direct dyes of formula (I) chosen from compounds (1) to (7) as defined previously, the geometrical or optical isomer forms thereof, the tautomers thereof, the organic or mineral acid or base salts thereof, or the solvates thereof such as hydrates, and also mixtures thereof.

According to another particular embodiment, the cosmetic composition comprises one or more azomethine direct dyes of formula (II) chosen from compounds (1') to (7) as defined previously, the geometrical or optical isomer forms thereof, the tautomers thereof, the organic or mineral, acid or base salts thereof, or the solvates thereof such as hydrates, and also mixtures thereof.

According to another particular embodiment, the cosmetic composition according to the invention also comprises one or more chemical oxidizing agents, chosen in particular from hydrogen peroxide, urea peroxide, alkali metal bromates, persalts such as perborates and persulfates, peracids, and oxidase enzymes (with the possible cofactors thereof), among which mention may be made of peroxidases, 2-electron oxidoreductases such as uricases, and 4-electron oxygenases, for instance laccases, and preferably, the chemical oxidizing agent is hydrogen peroxide.

According to one variant of the invention, the cosmetic composition is a ready-to-use cosmetic composition, especially for dyeing keratin fibres, in particular human keratin fibres such as the hair, which results from the mixing of a cosmetic composition comprising one or more compounds of the abovementioned formula (I) and/or (II) and a cosmetic composition comprising one or more chemical oxidizing agents, as described previously.

According to another variant of the invention, the cosmetic composition does not comprise any chemical oxidizing agent. When the cosmetic composition does not comprise any chemical oxidizing agent, dyeing of the keratin fibres using the leuco compounds of formula (II) is performed with atmospheric oxygen. Simple exposure to air of the treated keratin fibres, especially human keratin fibres such as the hair, with the composition comprising the compound(s) of leuco type makes it possible to generate the colouring species and, consequently, to dye the fibres.

The direct dye(s) as defined previously may be present in the cosmetic composition according to the invention in a content ranging from 0.001% to 10% by weight, preferably in a content ranging from 0.005% to 6% by weight and preferentially in a content ranging from 0.1% to 1% relative to the total weight of the cosmetic composition.

The cosmetic composition according to the invention may also comprise one or more additional dyes chosen from oxidation dyes.

The oxidation dyes are generally chosen from one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the corresponding addition salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline. N,N-bis(i-hydroxyethyl)-para-phenylenediamine, 4-N,N-bis(0-hydroxyethyl)amino-2-methylaniline, 4-N,N-bis(p-hydroxyethyl)amino-2-chloroaniline, 2-1-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-paraphenylenediamine, N-ethyl-N-((β-hydroxyethyl)-para-phenylenediamine, N-((β,γ-dihydroxypropyl)-para-phenylenediamine, N-(4'-aminophenyl)-para-phenylenediamine, N-phenyl-para-phenylenediamine, 2-β-hydroxyethyloxy-para-phenylenecliamine, 2-β-acetylaminoethyloxy-para-phenylenediamine, N-((β-methoxyethyl)-para-phenylenediamine, 4-aminophenylpyrrolicline. 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis((β-hydroxyethyl)-para-phenylenediamine, 2-chloro-para-phenylenediamine and 2-β-acetylaminoethyloxy-para-phenylenediamine, and the corresponding addition salts with an acid, are particularly preferred, Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis((β-hydroxyethyl)-N,N'-bis(4-aminophenyptetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-β-hydroxyethyl-aminomethyl)phenol and 4-amino-2-fluorophenol, and the corresponding addition salts with an acid.

Among the ortho-aminophenols that may be mentioned, for example, are 2-aminophenol, 2-amino-5-methylphenol. 2-amino-6-methylphenol and 5-acetamido-2-aminophenol, and the corresponding addition salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-ypethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-yiamine, 2-[(3-aminopyrazolo[1,5-a]pyrid-5-yl)(2-hydroxyethyl)amino]ethanol. 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-6-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$) alkylpiperazinium group; or c) a ($C_1$-$C_6$)alkoxy group optionally substituted with one or more hydroxyl groups, such as a β-hydroxyakoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine. 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamine-1-(0-hydroxyethyl)pyrazoie, 3,4-diaminopyrazole, 4,5-diamino-1-(4"-chlarobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamine-3-methylpyrazole, 4,5-diamino-3-tert-butyl-1-methylpyrazole, 4,5-diamino-1-ted-butyl-3-methylpyrazole, hydroxyethyl)-3-methylpyrazole, 4,5-diamino-1-ethyl-3-methylpyrazole. 4,5-diamino-1-ethyl-3-(4'-methoxyphenyl)pyrazole, 4,5-diamino-1-ethyl-3-hydraxymethylpyrazole, 4,5-diamino-3-hydroxymethyi-1-methylpyrazole, 4,5-diamino-3-hydroxymettlyi-1-isopropylpyrazole. 4,5-diamino-3-methyl-1-isopropylpyrazole, 4-amino-5-(2' aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(6-hydroxyethyl)amino-1-methylpyrazole, and the corresponding addition salts. Use may also be made of 4,5-diamino-1-(f3-methoxyethyl)pyrazole A 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-clihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H.5H-pyrazolo[1,2-a]pyrazol-1-one, 2-amino-3-(pyrrolidin-1-0-6,7-dihydro-1H, 5H-pyrazolo[1,2-a]pyrazol-1-one, 4,5-diamine-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolop,2-alpyrazol-1-one. 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazoi-3-one, 4-amino-5-(3-dimethylaminopyrrolidin-1-yl)-1,2-diethyl-1,2-dihydropyrazol-3-one and 2,3-cliamino-6-hydroxy-6,7-dihydro-1H,5H-pyrazolo[1,2-a]pyrazol-1-one Use will preferably be made of 2,3-diamino-6,7-dihydro-1H,5H-pyrazolo[1,2-a]pyrazol-1-one and/or a corresponding salt.

Heterocyclic bases that will preferably be used are 4,5-diamino-1-(β-hydroxyethyopyrazole and/or 2,3-diamino-6,7-dihydro-1H,5H-pyrazolo[1,2-a]pyrazoi-1-one and/or a corresponding salt.

The composition according to the invention may optionally comprise one or more coupling agents advantageously chosen from those conventionally used in the dyeing of keratin fibres.

Among these coupling agents, mention may be made in particular of meta-phenylenediamines, meta-aminophenols, meta-diphenols, naphthalene-based coupling agents and heterocyclic coupling agents, and also the corresponding addition salts.

Mention may be made, for example, of 1,3-dihydroxybenzene. 1,3-dihydroxy-2-methylbenzene, 4-chloro-1,3-dihydroxybenzene, 2,4-diamino-1-(β-hydroxyethyloxy)benzene, 2-amino-4-(3-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxylndole, 4-hydroxy-N-methylindole, 2-amino-3-hydroxypyridine, 6-hydroxybenzomorpholine, dimethoxypyridine, 1-N-(β-hydroxyethyl)amino-3,4-methylenedioxybenzene, 2,6-bis (β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]- 1,2,4-triazole, 2,6-dinnethyl[3,2-c]-1,2,4-triazole and 6-methylpyrazolo[1,5-a]benzimidazole, 2-methyl-5-amino-phenol, 5-N-(β-hydroxyethyl)amino-2-methylphenol, 3-aminophenol and 3-amino-2-chloro-6-methyiphenol, the corresponding addition salts with an acid and the corresponding mixtures.

In general, the addition salts of oxidation bases and couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the composition and of the ready-to-use composition.

The coupler(s), if it (they) are present, each advantageously represent from 0.001% to 10% by weight relative to the total weight of the composition, and preferably from 0.005% to 5% by weight relative to the total weight of the composition and of the ready-to-use composition.

The composition according to the invention may optionally comprise b) one or more synthetic or natural direct dyes chosen from cationic, anionic and nonionic species, preferably cationic and nonionic species, either as sole dyes or in addition to the additional oxidation dye(s).

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (111a) and (III'a), the azo cationic dyes (IVa) and (IV'a) and the diazo cationic dyes (Va) below:

(IIIa)

An⁻

(III'a)

(IVa)

(IV'a)     and

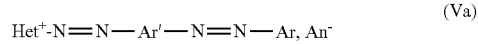
(Va)

in which formulae (IIIa), (III'a), (IVa), (IV'a) and (Va):

Her represents a cationic heteroaryl radical, preferably bearing an endocyclic cationic charge, such as imidazolium, indolium or pyridinium, optionally substituted preferably with one or more $(C_1-C_8)$alkyl groups such as methyl;

$Ar^+$ represents an aryl radical, such as phenyl or naphthyl, bearing an exocyclic cationic charge, preferably ammonium, particularly tri$(C_1-C_8)$alkylammonium such as trimethylammoniun;

Ar represents an aryl group, in particular phenyl, which is optionally substituted, preferably with one or more electron-donating groups such as i) optionally substituted $(C_1-C_8)$ alkyl, ii) optionally substituted $(C_1-C_6)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or, as a variant, Ar represents a julolidine group;

Ar' represents an optionally substituted divalent (hetero) arylene group such as phenylene, particularly para-phenylene, or naphthalene, which is optionally substituted, preferably with one or more $(C_1-C_8)$alkyl, hydroxyl or $(C_1-C_8)$alkoxy groups;

Ar" represents an optionally substituted (hetero)aryl group such as phenyl or pyrazolyl, which are optionally substituted, preferably with one or more $(C_1-C_8)$alkyl, hydroxyl, (di)$(C_1-C_8)$(alkyl)amino, $(C_1-C_8)$alkoxy or phenyl groups;

$R^a$ and $R^b$, which may be identical or different, represent a hydrogen atom or a $(C_1-C_8)$alkyl group, which is optionally substituted, preferably with a hydroxyl group, or, as a variant, the substituent Ra with a substituent of Het⁺ and/or $R^b$ with a substituent of Ar and/or $R^a$ with $R^b$ form, together with the atoms that bear them, a (hetero)cycloalkyl;

in particular, $R^a$ and $R^b$ represent a hydrogen atom or a $(C_1-C_4)$alkyl group, which is optionally substituted with a hydroxyl group;

An⁻ represents an anionic counterion, such as mesylate or halide.

Mention may be made in particular of azo and hydrazone cationic dyes bearing an endocyclic cationic charge of formulae (IIIa), (III'a) and (IVa) as defined previously. More particularly, those of formulae (IIIa), (III'a) and (IVa) derived from the dyes described in patent applications WO 95/15144, WO 95/01772 and EP-714954.

Preferably, the cationic part is derived from the following derivatives:

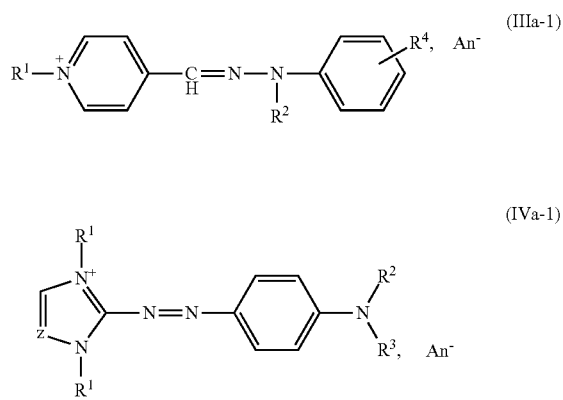

formulae (IIIa-1) and (IVa-1) with:

$R^1$ representing a $(C_1\text{-}C_4)$alkyl group such as methyl;

$R^2$ and $R^3$, which may be identical or different, representing a hydrogen atom or a $(C_1\text{-}C_4)$alkyl group, such as methyl; and $R^4$ representing a hydrogen atom or an electron-donating group such as an optionally substituted $(C_1\text{-}C_8)$alkyl group, an optionally substituted $(C_1\text{-}C_8)$alkoxy group, or a $(di)(C_1\text{-}C_8\text{ (alkyl)}$amino group optionally substituted on the alkyl group(s) with a hydroxyl group; in particular, $R^4$ represents a hydrogen atom, Z represents a CH group or a nitrogen atom, preferably CH, An⁻ represents an anionic counterion, such as mesylate or halide.

In particular, the dye of formulae (IIIa-1) and (IVa-1) is chosen from Basic Red 51. Basic Yellow 87 and Basic Orange 31 or corresponding derivatives:

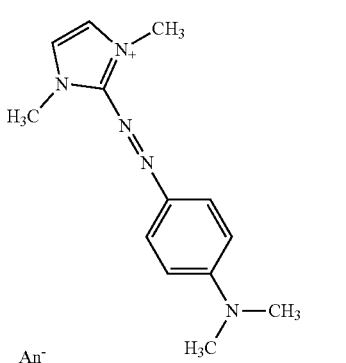

Basic Red 51

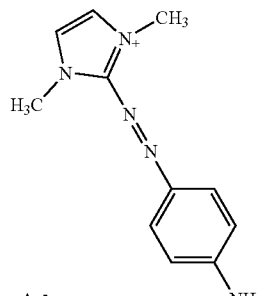

Basic Orange 31

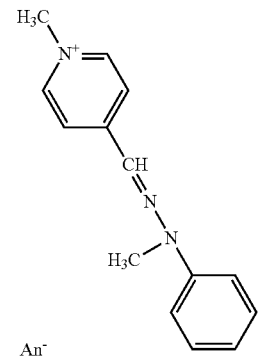

Basic Yellow 87

Among the natural direct dyes that may be used according to the invention, mention may be made of hennotannic acid, juglone, alizarin, purpurin, carminic acid, kermesic acid, purpurogallin, protocatechaldehyde, indigo, isatin, curcumin, spinulosin, apigenidin and orcein. Extracts or decoctions containing these natural dyes and in particular henna-based poultices or extracts may also be used.

When they are present, the direct dye(s) more particularly represent from 0.001% to 10% by weight and preferably from 0.005% to 5% by weight relative to the total weight of the composition.

The cosmetic composition according to the invention may be present in various forms, such as in the form of liquids, creams, gels, or any other form that is suitable for dyeing keratin fibres, and especially human hair.

As indicated previously, the invention also relates to the use of the cosmetic composition as defined previously, optionally in the presence of chemical oxidizing agents, for dyeing keratin fibres, in particular human keratin fibres such as the hair.

IV. Dyeing Device

The present invention also relates to a single-compartment or multi-compartment device or "kit" comprising a first compartment containing one or more compounds of formula (I) and/or (II), and optionally a second compartment containing one or more chemical oxidizing agents as defined above.

For the purposes of the invention, the term "multi-compartment" means that the device comprises at least two compartments.

In particular, the invention relates to a multi-compartment dyeing device or dyeing "kit" comprising a first compartment containing a cosmetic composition comprising one or more direct dyes of formula (I) and/or (II) as defined previously, and a second compartment comprising one or more chemical oxidizing agents as defined previously.

More particularly, the invention relates to a multi-compartment dyeing device or dyeing kit comprising a first compartment containing a cosmetic composition comprising one or more dyes of formula (I) as defined previously, free of chemical oxidizing agent, and a second compartment containing a cosmetic composition comprising one or more chemical oxidizing agents.

According to a particular embodiment, the device comprises at least one compartment comprising a cosmetic composition comprising one or more compounds of the abovementioned formula (I).

According to another particular embodiment, the multi-compartment dyeing device or dyeing kit comprises a first compartment containing a cosmetic composition comprising one or more compounds of leuco type of the abovementioned formula (II), and a second compartment containing a cosmetic composition comprising one or more chemical oxidizing agents.

According to another particular embodiment, the device comprises at least one compartment comprising a cosmetic composition comprising one or more compounds of leuco type of the abovementioned formula (II). In this case, the composition comprising the compound(s) of leuco type of formula (II) is applied to the keratin fibres, which become coloured due to their exposure to air.

According to one variant of the invention, the device comprises at least one compartment comprising a ready-to-use cosmetic composition which results from the mixing of a cosmetic composition comprising one or more compounds of the abovementioned formula (I) and/or (II) and a cosmetic composition comprising one or more chemical oxidizing agents, as described previously.

The devices mentioned above are suitable far dyeing keratin fibres.

The invention also relates to the use of one or more compounds of formula (I) and/or (II), optionally in the presence of one or more chemical oxidizing agents as defined previously, for dyeing keratin fibres, in particular human keratin fibres such as the hair.

The examples below are given to illustrate the invention and do not in any way limit the scope thereof.

The compounds were fully characterized via standard spectroscopic or spectrometric methods known to those skilled in the art,

SYNTHESIS EXAMPLES

Synthesis of 2-[{4-[2-amino-5-{44-(bis(2-hydroxy-ethyl)amino]phenylamino}-4-iminocyciohexa-2,5-dien-(Z)-ylideneamino]phenyl}(2-hydroxyethyl)amino]ethanal (a)

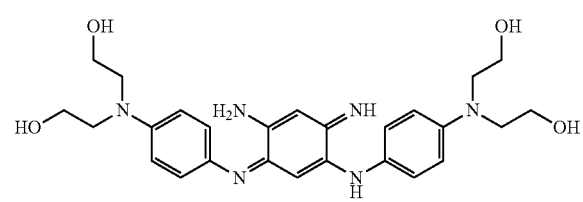 [SMILES: N=C1C=C(N)/C(=N\c2ccc(N(CCO)CCO)cc2)C=C1Nc1ccc(N(CCO)CCO)cc1]

Synthesis of 2,2',2"2'''-(4,6-dinitrobenzene-1,3-diyl)bis(iminobenzene-4,1-diylnitrilo)tetraethanol (1a)

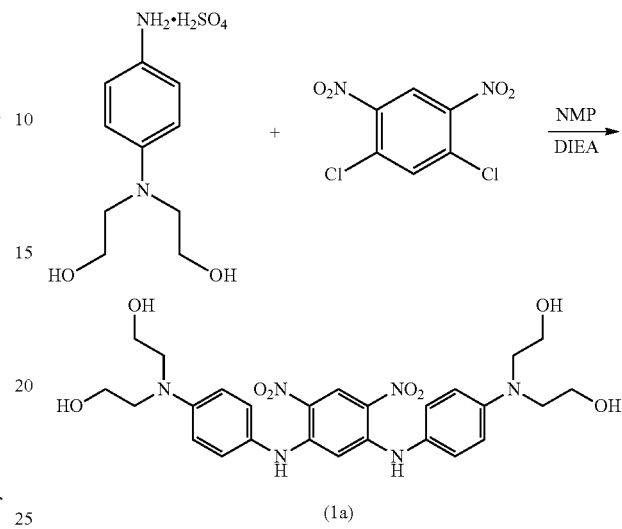

21.10 mmol of 1,5-dichloro-2,4-dinitrobenzene (5.0 g, 1 equivalent), 43.25 mmol of 2,2'-[(4-aminophenyl)imino]diethanol sulfate (13.51 g, 2.05 equivalents), 126.6 mmol of diisopropylethyiamine (22 ml, 6 equivalents) and 25 ml of 1-methyl-2-pyrrolidinone are placed in a 250 ml three-necked flask under an inert atmosphere. The reaction medium is heated to 100'C and the reaction is monitored by HPLC. After 3 hours at 100° C., the heating is stopped and the reaction medium is then poured onto ice. The insoluble brown matter formed is filtered off on a sinter, washed with 3×250 ml of water, suction-filtered then dried in a desiccator ($P_2O_5$, vacuum, 40° C.) to reach compound (1a) in the form of a dark red solid.

The NMR and mass spectrometry analyses are in accordance with the expected structure (1a).

11) Synthesis of 2-10-02-amino-5-(14-ibis(2-hydroxyethvijaminalphenAamino)-4-iminocyciohexa-2,5-dien-1-ylidenelaminWphenyl)(2-hydroxyethyl-aminolethanol (a)

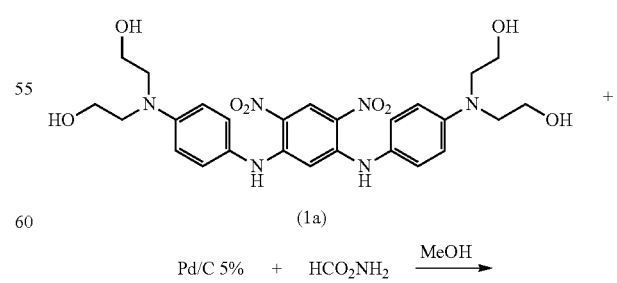

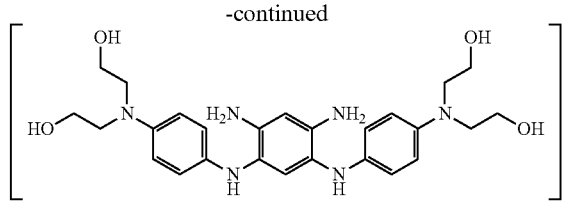

product not isolated

↓ oxidation in air

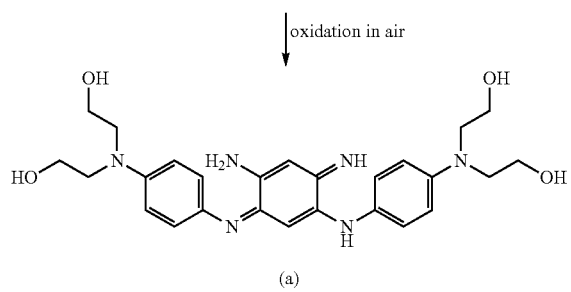

(a)

3.59 mmol of compound (1a) (2.0 g, 1 equivalent) and 1.0 g of 5% palladium on charcoal are introduced into a 100 ml three-necked flask under an inert atmosphere containing 25 ml of methanol. The reaction medium is heated to 65° C., 35.93 mmol of ammonium formate (2.26 g, 10 equivalents) are then added portionwise to the reaction medium and the reaction is monitored by TLC (dichloromethane/methanol: 95/5). After 2 hours at 65° C., the reaction medium is filtered through a sinter packed with Celite and the filtrate is then evaporated. The black solid obtained is then purified by chromatography on neutral alumina using an eluent constituted of a mixture of dichloromethane and methanol. Compound (a) is obtained in the form of a black solid.

The NMR and mass spectrometry analyses are in accordance with the expected structure (a).

EXAMPLES OF DYEING EVALUATION

Cosmetic composition 1 was prepared:

| Composition 1 | Mass content |
|---|---|
| Compound (a) | 500 mg |
| Water | 79.5 g |
| Ethanol | 15 g |
| Benzyl alcohol | 5 g |

2.0 g of composition 1 are applied to a lock of 1.0 g of grey hair containing 90% white hair After a leave-on time of 30 minutes at room temperature, the lock is rinsed, washed with a standard shampoo and then dried.

Spectrocolorimetric Evaluation

The colour of the locks was evaluated in the CIE L* a* b* system using a Minolta Spectrophotometer CM3610D colorimeter. In this L* a* b* system, the three parameters respectively denote the intensity of the colour (L*), the green/red colour axis (a*) and the blue/yellow colour axis (b*)

Colour Build-Up

The variation in colouration between the non-dyed and dyed locks of hair is defined by ($\Delta E^*$) according to the following equation:

$$\Delta E^* = \sqrt{(L^* - L_0^*)^2 + (a^* - a_0^*)^2 + (b^* - b_0^*)^2}$$

In this equation. L*, a* and b* represent the values measured on locks of hair after dyeing and $L_0^*$, $a_0^*$ and $b_0^*$ represent the values measured on locks of hair before dyeing. The higher the value of $\Delta E^*$, the greater the colour build-up.

Results

We obtain the following results:

| Composition 1 |
|---|
| L* = 25.03 |
| a* = 1.43 |
| b* = −5.73 |
| $\Delta E^*$ = 42.36 |
| Dark purple |

It is seen through these results that composition 1 according to the invention gives an intense, chromatic hair colouring and good colour build-up.

COMPARATIVE EXAMPLES

The following dye compositions A (comparative) and B (invention) were prepared from the ingredients mentioned in the table below. The contents are expressed as percentages of active material in a relative to the total weight of the composition 100 g.

Compound 1

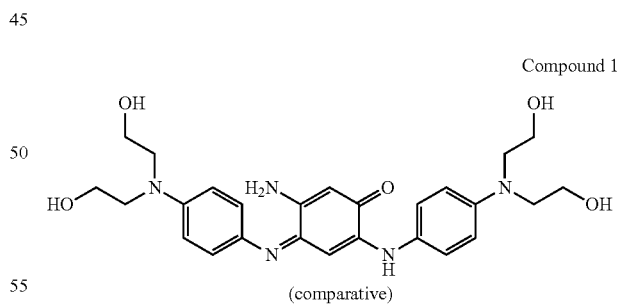

(comparative)

Compound 2

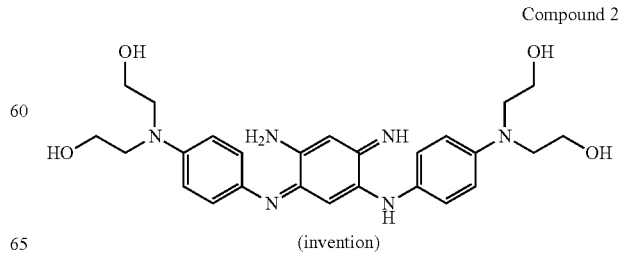

(invention)

|  | Composition A (comparative) | Composition B (invention) |
|---|---|---|
| Compound 1 | 0.5 | — |
| Compound 2 | — | 0.5 |
| Pure ethyl alcohol | 15 | 15 |
| Benzyl alcohol | 5 | 5 |
| Water | 79.5 | 79.5 |

Process 2 g of each of the compositions are applied to 1 g locks of natural Caucasian hair containing 90% white hairs. After 30 minutes, the locks are rinsed, shampooed and then dried. The colorimetric data of each of the locks are then measured with a Minolta CM-3610d spectrophotometer.

Results

The results are given in the table below.

| Compositions tested | L* | ΔE |
|---|---|---|
| Composition A (comparative) | 49.90 | 12.71 |
| Composition B (invention) | 25.03 | 42.36 |

It is seen from the above table that the colour obtained with the comparative composition A (very very light grey) is significantly lighter than that obtained with composition B according to the invention. Furthermore, the colour build-up is significantly weaker for the comparative composition than for that obtained with the composition according to the invention.

The invention claimed is:

1. A method for dyeing keratin fibers, comprising applying to said keratin fibers a composition comprising at least one compound selected from compounds of formula (I) or (II) below, organic or mineral acid or base salts thereof, tautomers thereof, optical isomers thereof, geometrical isomers thereof, or solvates thereof:

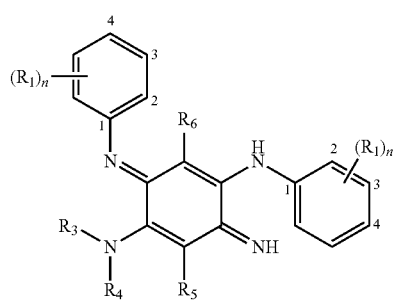

(I)

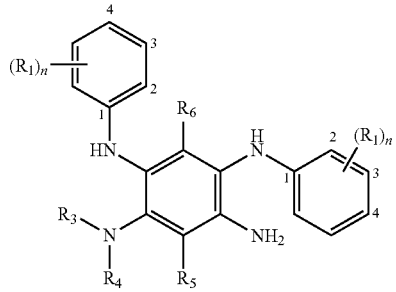

(II)

wherein formulae (I) and (II):
n represents an integer equal to 0, 1, 2, 3, 4 or 5;
$R_1$ represents:
a halogen atom,
a sulfonic radical —$SO_3H$ or sulfonate radical —$SO_3^-$, $M^+$;
a carboxyl radical —$CO_2H$, a carboxylate radical —$COO^-$;
an aromatic or non-aromatic, 5- to 10-membered cationic heterocycle, which is optionally substituted with one or more identical or different radicals chosen from $C_1$-$C_4$ alkyl and $C_1$-$C_4$ hydroxyalkyl;
an aromatic or non-aromatic, 5- to 6-membered non-cationic heterocycle, substituted with:
an ammonium radical —$N^+RR'R''$ with R, R' and R'', which may be identical or different, representing a ($C_1$-$C_4$)alkyl group optionally substituted with one or more hydroxyl groups, or
an aromatic or non-aromatic, 5- to 10-membered cationic heterocycle, which is optionally substituted with one or more identical or different radicals chosen from $C_1$-$C_4$ alkyl and $C_1$-$C_4$ hydroxyalkyl,
an ammonium radical —$N^+RR'R''$, wherein R, R' and R'', which may be identical or different, represent a $C_1$-$C_4$ alkyl group, or
a radical —W—$R_7$, wherein:
W represents:
an oxygen or sulfur atom,
a divalent group —N($R_8$)— or
a linear or branched, saturated or unsaturated, divalent hydrocarbon-based chain, comprising from 1 to 14 carbon atoms, said hydrocarbon-based chain being:
optionally substituted with one or more radicals, which may be identical or different, chosen from the following radicals: i) hydroxyl, ii) (di)($C_1$-$C_6$)(alkyl)amino, iii) ammoniums —$N^+RR'R''$, iv) aromatic or non-aromatic, optionally substituted, 5- to 10-membered cationic heterocycles, v) aromatic or non-aromatic, 5- or 6-membered non-cationic heterocycles, substituted with one or more radicals, which may be identical or different, chosen from the following radicals: a) ammonium —$N^+RR'R''$, and b), aromatic or non-aromatic, 5- to 10-membered cationic heterocycle, optionally substituted with one or more identical or different radicals chosen from $C_1$-$C_4$ alkyl;
and/or optionally interrupted, optionally starting, and/or optionally terminating with one or more divalent heteroatoms or groups, which may be identical or different, chosen from:
—O—, —S—, —N($R_{10}$)—, —S(O)—, —S(O)$_2$—, and —C(X)— with X representing an oxygen or sulfur atom or a group N$R_{10}$ and $R_{10}$ representing a hydrogen atom or a ($C_1$-$C_6$) alkyl group, and
combinations thereof;
$R_7$ and $R_8$, which may be identical or different, represent:
a hydrogen atom,
a linear or branched $C_1$-$C_{14}$ alkyl group, said alkyl group being:
optionally interrupted with one or more heteroatoms or groups selected from —O—, —S—, —N($R_{10}$)—, —S(O)—, —S(O)$_2$—, —C(X)—, or combinations thereof; or
optionally substituted with one or more radicals, which may be identical or different, chosen from the following radicals: i) hydroxyl, ii) (di)($C_1$-$C_6$)(alkyl)amino, iii) ammoniums —N$^+$RR'R", iv) aromatic or non-aromatic, optionally substituted, 5- to 10-membered cationic heterocycles, v) aromatic or non-aromatic, 5- or 6-membered non-cationic heterocycles, substituted with one or more radicals, which may be identical or different, chosen from the following radicals: a) ammonium —N$^+$RR'R", or b), aromatic or non-aromatic, 5- to 10-membered cationic heterocycle, optionally substituted with one or more identical or different radicals chosen from $C_1$-$C_4$ alkyl; $R_3$ and $R_4$, which may be identical or different, representing a hydrogen atom;
$R_5$ and $R_6$, which may be identical or different, represent an atom or group chosen from:
a hydrogen atom,
a halogen atom,
a $C_1$-$C_6$ alkyl radical,
a ($C_1$-$C_6$)alkyl radical substituted with one or more radicals chosen from the following radicals: i) hydroxyl, ii) amino —NH$_2$, iii) ($C_1$-$C_6$)alkylamino, and iv) di($C_1$-$C_6$)alkylamino,
a ($C_1$-$C_6$)alkoxy radical, or
a ($C_1$-$C_6$)alkoxy radical substituted with one or more radicals chosen from the following radicals: i) hydroxyl, ii) amino, iii) ($C_1$-$C_6$)alkylamino, and iv) di($C_1$-$C_6$)alkylamino,
wherein:
the compounds of formulae (I) and (II) are symmetric,
when the compound of formula (I) or (II) is cationic, it optionally comprises one or more anions An$^-$ and optionally one or more cations M$^+$ to ensure the electrical neutrality of the molecule;
wherein:
An$^-$ denoting an anion chosen from bromide, chloride, a methylsulfate ion, a toluenesulfonate ion, or a mixture thereof;
M$^+$ representing a cation chosen from sodium, potassium, magnesium, calcium, or ammonium.

2. The method according to claim 1, further comprising: applying an oxidizing composition, wherein the oxidizing composition comprises at least one chemical oxidizing agent chosen from hydrogen peroxide, urea peroxide, alkali metal bromates, persalts, peracids, or oxidase enzymes; wherein the fibers are optionally rinsed, washed, or dried between the first and second steps.

3. The method according to claim 1, wherein the composition comprising the at least one compound of formula (I) and/or (II) further comprises at least one chemical oxidizing agent chosen from hydrogen peroxide, urea peroxide, alkali metal bromates, persalts, perborates, persulfates, peracids, or oxidase enzymes (with the optional cofactors thereof, wherein the method optionally further comprises at least one step chosen from rinsing, washing, or drying the keratin fibers.

4. The method according to claim 1, wherein $R_5$ and $R_6$ represent a hydrogen atom.

5. The method according to claim 1, wherein $R_1$ represents:
a sulfonic radical —SO$_3$H or sulfonate radical —SO$_3^-$, M$^+$;
a hydrogen atom;
a radical —W'—R'$_7$, wherein:
W' represents an oxygen or sulfur atom or a divalent group —N(R'$_8$)—;
R'$_7$ and R'$_8$, which may be identical or different, represent a linear or branched, saturated or unsaturated alkyl group, comprising from 1 to 8 carbon atoms, said hydrocarbon-based chain being:
optionally substituted with one or more radicals, which may be identical or different, chosen from the following radicals: i) hydroxyl, ii) (di)($C_1$-$C_6$)(alkyl)amino, iii) ammoniums —N$^+$RR'R", iv) aromatic or non-aromatic, 5- to 10-membered cationic heterocycles, optionally substituted with at least one ($C_1$-$C_4$)alkyl group chosen from ($C_1$-$C_4$)(alkyl)imidazoliums, ($C_1$-$C_4$)(alkyl)piperaziniums, ($C_1$-$C_4$)(alkyl)pyrrolidiniums, ($C_1$-$C_4$)(alkyl)piperidiniums, morpholiniums, v) aromatic or non-aromatic, 5- or 6-membered non-cationic heterocycles, substituted with a radical chosen from the following radicals: a) ammonium —N$^+$RR'R", An$^-$, and b), aromatic, 5- to 10-membered cationic heterocycle, optionally substituted with one or more radicals, which may be identical or different, chosen from $C_1$-$C_4$ alkyl; or
optionally interrupted with one or more divalent heteroatoms or groups, which may be identical or different, chosen from:
—O—, —N($R_{10}$)—, and —C(O)—, or combinations thereof;
R'$_7$, and R'$_8$, which may be identical or different, represent:
a hydrogen atom,
a linear or branched $C_1$-$C_{14}$, said alkyl group being:
optionally interrupted with at least one heteroatom or group, which may be identical or different, chosen from —O—, —S—, —N($R_{10}$)—, —S(O)—, —S(O)$_2$—, —C(X)—, or combinations thereof; or
optionally substituted with one or more radicals, which may be identical or different, chosen from the following radicals: i) hydroxyl, ii) (di)($C_1$-$C_6$)(alkyl)amino, iii) ammoniums —N$^+$RR'R", iv) aromatic or non-aromatic, optionally substituted, 5- to 10-membered cationic heterocycles, v) aromatic or non-aromatic, 5- or 6-membered non-cationic heterocycles, substituted with a radical chosen from the following radicals: a) ammonium —N$^+$RR'R", and b), aromatic or non-aromatic, 5- to 10-membered cationic heterocycle, optionally substituted with at least one identical or different radical chosen from $C_1$-$C_4$ alkyl;

n represents an integer equal to 0 or 1;

$R_3$ and $R_4$ represent a hydrogen atom;

$R_5$ and $R_6$ represent a hydrogen atom;

An⁻ is an anionic counterion chosen from bromide, chloride, methyl sulfate, toluenesulfonate ions, or a mixture of these ions.

6. The method according to claim 1, wherein $R_1$ represents:
   a radical —$OR_7$;
   a radical —$SR_7$;
   a radical —$NR_7R_8$;
   a linear or branched $C_1$-$C_{14}$ alkyl radical, said alkyl radical being:
      optionally interrupted with at least one heteroatom or group, which may be identical or different, chosen from —O—, —S—, —N(H)—, —N($R_{10}$)—, —S(O)—, S(O)$_2$,—C(X)— with X representing an oxygen or sulfur atom, or N—R, or combinations thereof; or
      optionally substituted with at least one radical, which may be identical or different, chosen from the following radicals: i) hydroxyl, ii) $C_1$-$C_4$ alkoxy, iii) amino —$NH_2$, iv) $C_1$-$C_6$ mono- or dialkylamino, v) ammoniums —N⁺RR'R", or vi) optionally substituted, aromatic or non-aromatic, 5- to 10-membered cationic heterocycles, vii) aromatic or non-aromatic, 5- or 6-membered non-cationic heterocycles, substituted with a radical chosen from the following radicals:
         ammoniums —N⁺RR'R", or
         optionally substituted, aromatic or non-aromatic, 5- to 10-membered cationic heterocycle;
         a hydroxyl, amino, $C_1$-$C_4$ alkylamino, $C_1$-$C_4$ dialkylamino, $C_1$-$C_4$ alkoxy, $C_1$-$C_4$ alkyl or $C_1$-$C_4$ hydroxyalkyl radical; or
   a linear or branched $C_1$-$C_{14}$, alkoxy radical, said alkoxy radical being:
      optionally interrupted with at least one heteroatom or group, which may be identical or different, chosen from —O—, —S—, —N($R_{10}$)—, —S(O)—, S(O)$_2$,—C(X)— with X representing an oxygen or sulfur atom, N—R, or a combination thereof; or
      optionally substituted with at least one radical, which may be identical or different, chosen from the following radicals: i) hydroxyl, ii) $C_1$-$C_4$ alkoxy, iii) amino —$NH_2$, iv) $C_1$-$C_6$ mono-/or dialkylamino, v) ammoniums —N⁺RR'R", vi) optionally substituted, aromatic or non-aromatic, 5- to 10-membered cationic heterocycles, or vii) aromatic or non-aromatic, 5- or 6-membered non-cationic heterocycles, substituted with a radical chosen from the following radicals:
         ammoniums —N⁺RR'R",
         optionally substituted, aromatic or non-aromatic, 5- to 10-membered cationic heterocycle; or
         a hydroxyl, amino, $C_1$-$C_4$ alkylamino, $C_1$-$C_4$ dialkylamino, $C_1$-$C_4$ alkoxy, $C_1$-$C_4$ alkyl, or $C_1$-$C_4$ hydroxyalkyl radical.

7. The method according to claim 1, wherein n represents an integer equal to 1, and $R_1$ is in position 4.

8. The method according to claim 1, wherein the at least one cationic heterocycle is chosen from imidazoliums, piperaziniums, pyrrolidiniums, morpholiniums, or piperidiniums; optionally substituted with one or more radicals, which may be identical or different, chosen from (hydroxy)($C_1$-$C_4$)alkyl radicals.

9. The method according to claim 1, characterized in that said at least one non-cationic heterocycle is 5- or 6-membered and is chosen from piperidines, piperazines, pyrrolidines, morpholines, thiazoles, imidazoles, or pyridines, the 5- or 6-membered non-cationic heterocycles optionally substituted with:
   an ammonium radical —N⁺RR'R" with R, R' and R", which may be identical or different, representing a ($C_1$-$C_4$)alkyl group optionally substituted with at least one hydroxyl group, or
   an aromatic or non-aromatic, 5- to 10-membered cationic heterocycle, which is optionally substituted with one or more identical or different radicals chosen from (hydroxy)($C_1$-$C_4$)alkyl radicals.

10. The method according to claim 1, wherein the at least one non-cationic heterocycle is a pyrrolidine substituted with:
    one or more identical or different ammonium radicals —N⁺RR'R", or
    an aromatic or non-aromatic, 5- to 10-membered cationic heterocycle, optionally substituted with at least one (hydroxy)($C_1$-$C_4$)alkyl group.

11. The method according to any one of the preceding claims, wherein $R_1$ represents a group chosen from:
    hydroxyl,
    a sulfonic radical —$SO_3H$ or sulfonate radical —$SO_3^-$,
    amino,
    (di)(hydroxy)($C_1$-$C_6$)alkylamino,
    (hydroxy)($C_1$-$C_6$)alkoxy, or
    (di)(alkoxy)alkylamino.

12. The method according to claim 1, wherein the compounds of formulae (I) or (II) are chosen from the compounds (1) to (7) and (1') to (7'), geometrical or optical isomers thereof, tautomers thereof, organic or mineral acid or base salts thereof, or solvates thereof:

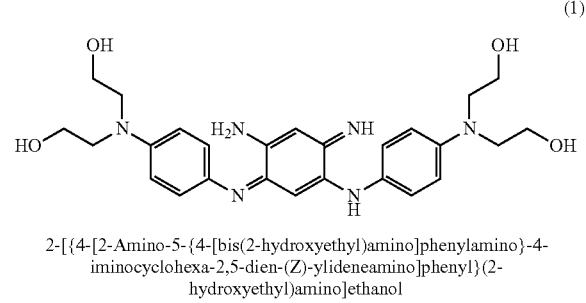

(1)

2-[{4-[2-Amino-5-{4-[bis(2-hydroxyethyl)amino]phenylamino}-4-iminocyclohexa-2,5-dien-(Z)-ylideneamino]phenyl}(2-hydroxyethyl)amino]ethanol

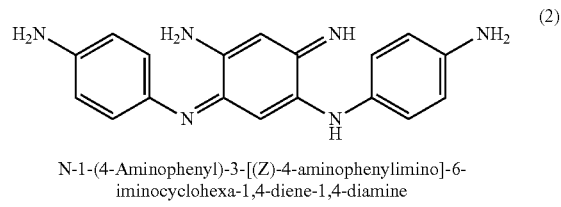

(2)

N-1-(4-Aminophenyl)-3-[(Z)-4-aminophenylimino]-6-iminocyclohexa-1,4-diene-1,4-diamine

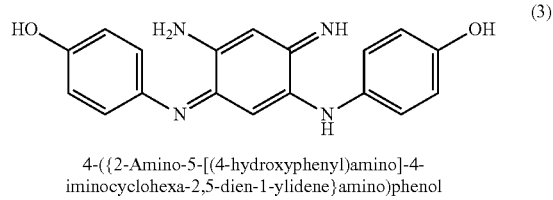

(3)

4-({2-Amino-5-[(4-hydroxyphenyl)amino]-4-iminocyclohexa-2,5-dien-1-ylidene}amino)phenol

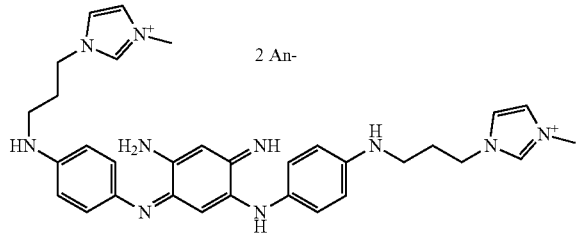

(4)

Salt of 1-(3-{[4-({2-amino-4-imino-5-[(4-{[3-(3-methyl-1H-imidazol-3-ium-1-yl)propyl]amino}phenyl)amino]cyclohexa-2,5-dien-1-ylidene}amino)phenyl]amino}propyl)-3-methyl-1H-imidazol-3-ium 2 An⁻

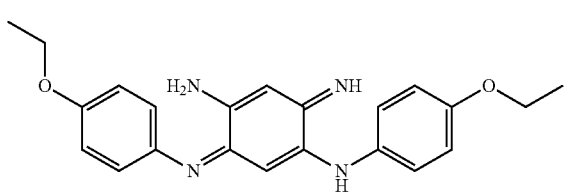

(5)

N-1-(4-Ethoxyphenyl)-3-[4-ethoxyphenylimino]-6-iminocyclohexa-1,4-diene-1,4-diamine

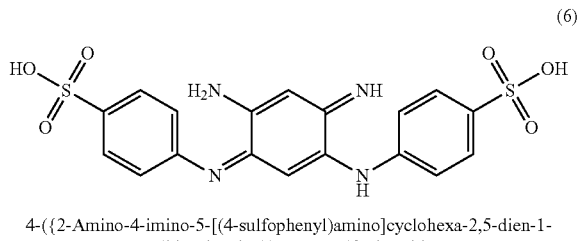

(6)

4-({2-Amino-4-imino-5-[(4-sulfophenyl)amino]cyclohexa-2,5-dien-1-ylidene}amino)benzenesulfonic acid

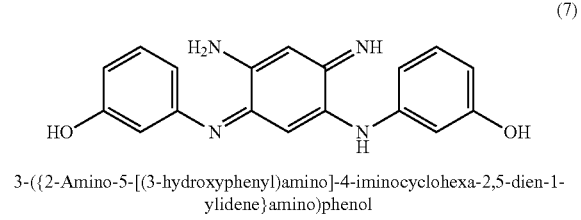

(7)

3-({2-Amino-5-[(3-hydroxyphenyl)amino]-4-iminocyclohexa-2,5-dien-1-ylidene}amino)phenol

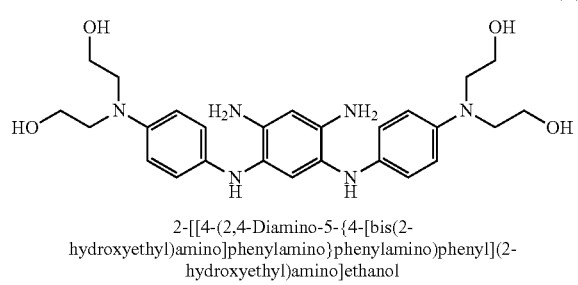

(1′)

2-[[4-(2,4-Diamino-5-{4-[bis(2-hydroxyethyl)amino]phenylamino}phenylamino)phenyl](2-hydroxyethyl)amino]ethanol

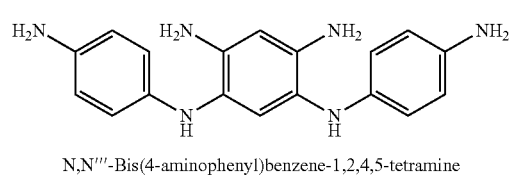

(2′)

N,N‴-Bis(4-aminophenyl)benzene-1,2,4,5-tetramine

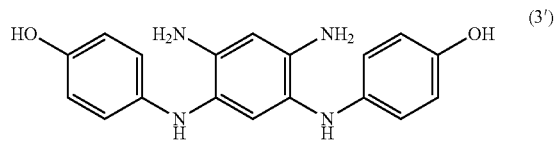

(3′)

N,N‴-Bis(4-hydroxyphenyl)benzene-1,2,4,5-tetramine

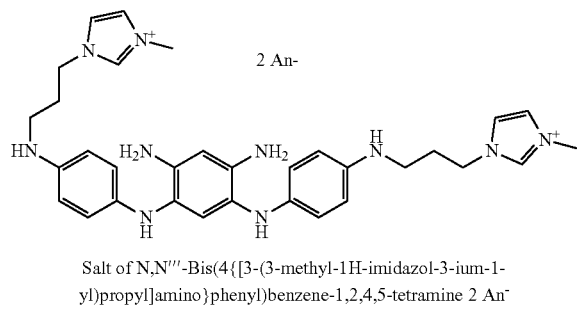

(4′)

Salt of N,N‴-Bis(4{[3-(3-methyl-1H-imidazol-3-ium-1-yl)propyl]amino}phenyl)benzene-1,2,4,5-tetramine 2 An⁻

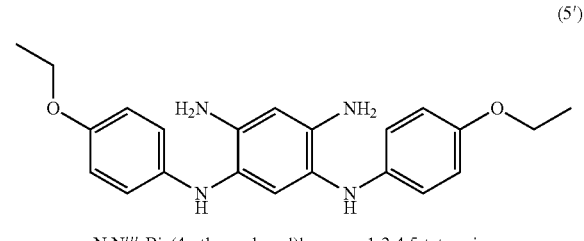

(5′)

N,N‴-Bis(4-ethoxyphenyl)benzene-1,2,4,5-tetramine

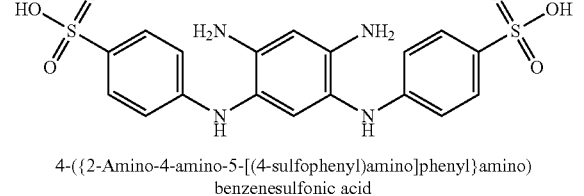

(6′)

4-({2-Amino-4-amino-5-[(4-sulfophenyl)amino]phenyl}amino)benzenesulfonic acid

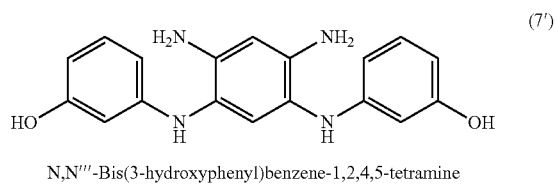

(7′)

N,N‴-Bis(3-hydroxyphenyl)benzene-1,2,4,5-tetramine wherein An⁻ is an anion chosen from bromide, chloride, a methylsulfate ion, a toluenesulfonate ion, or a mixture thereof.

13. A compound of formula (I) or (II) below, an organic or mineral, acid or base salt thereof, a tautomer thereof, an optical isomer or geometrical isomer thereof, or a solvate thereof:

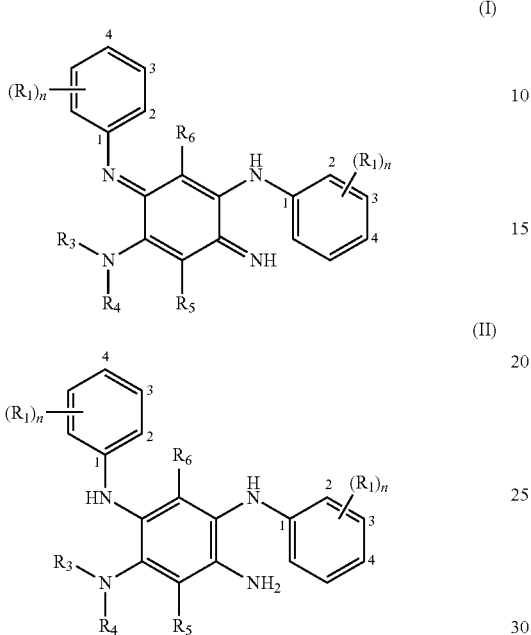

wherein formulae (I) and (II):
n represents an integer equal to 0, 1, 2, 3, 4 or 5; prefer represents 0 or 1;
$R_1$ represents:
a halogen atom,
a sulfonic radical —$SO_3H$ or sulfonate radical —$SO_3^-$, $M^+$;
a carboxyl radical —$CO_2H$, a carboxylate radical —$COO^-$;
an aromatic or non-aromatic, 5- to 10-membered cationic heterocycle, which is optionally substituted with one or more identical or different radicals chosen from $C_1$-$C_4$ alkyl and $C_1$-$C_4$ hydroxyalkyl;
an aromatic or non-aromatic, 5- to 6-membered non-cationic heterocycle, substituted with:
an ammonium radical —$N^+RR'R''$ with R, R' and R'', which may be identical or different, representing a ($C_1$-$C_4$)alkyl group optionally substituted with one or more hydroxyl groups, or
an aromatic or non-aromatic, 5- to 10-membered cationic heterocycle, which is optionally substituted with one or more identical or different radicals chosen from $C_1$-$C_4$ alkyl and $C_1$-$C_4$ hydroxyalkyl,
an ammonium radical —$N^+RR'R''$, wherein R, R' and R'', which may be identical or different, represent a $C_1$-$C_4$ alkyl group, or
a radical —W—$R_7$, wherein:
W represents:
an oxygen or sulfur atom,
a divalent group —N($R_8$)— or
a linear or branched, saturated or unsaturated, divalent hydrocarbon-based chain, comprising from 1 to 14 carbon atoms, said hydrocarbon-based chain being:
optionally substituted with one or more radicals, which may be identical or different, chosen from the following radicals: i) hydroxyl, ii) (di)($C_1$-$C_6$)(alkyl)amino, iii) ammoniums —$N^+RR'R''$, iv) aromatic or non-aromatic, optionally substituted, 5- to 10-membered cationic heterocycles, v) aromatic or non-aromatic, 5- or 6-membered non-cationic heterocycles, substituted with one or more radicals, which may be identical or different, chosen from the following radicals: a) ammonium —$N^+RR'R''$, and b), aromatic or non-aromatic, 5- to 10-membered cationic heterocycle, optionally substituted with one or more identical or different radicals chosen from $C_1$-$C_4$ alkyl;
and/or
optionally interrupted, optionally starting and optionally terminating with one or more divalent heteroatoms or groups, which may be identical or different, chosen from:
—O—, —S—, —N($R_{10}$)—, —S(O)—, —S(O)$_2$—, and —C(X)— with X representing an oxygen or sulfur atom or a group $NR_{10}$ and $R_{10}$ representing a hydrogen atom or a ($C_1$-$C_6$) alkyl group, and
combinations thereof;
$R_7$ and $R_8$, which may be identical or different, represent:
a hydrogen atom,
a linear or branched $C_1$-$C_6$ alkyl group, said alkyl group being:
optionally interrupted with one or more heteroatoms or groups selected from —O—, —S—, —N($R_{10}$)—, —S(O)—, —S(O)$_2$—, —C(X)—, or combinations thereof; or
optionally substituted with one or more radicals, which may be identical or different, chosen from the following radicals: i) hydroxyl, ii) (di)($C_1$-$C_6$)(alkyl)amino, iii) ammoniums —$N^+RR'UR''$, iv) aromatic or non-aromatic, optionally substituted, 5- to 10-membered cationic heterocycles, v) aromatic or non-aromatic, 5- or 6-membered non-cationic heterocycles, substituted with one or more radicals, which may be identical or different, chosen from the following radicals: a) ammonium —$N^+RR'R''$, or b), aromatic or non-aromatic, 5- to 10-membered cationic heterocycle, optionally substituted especially with one or more identical or different radicals chosen from $C_1$-$C_4$ alkyl; $R_3$ and $R_4$, which may be identical or different, representing a hydrogen atom;
$R_5$ and $R_6$, which may be identical or different, represent an atom or group chosen from:
a hydrogen atom,
a halogen atom,
a $C_1$-$C_6$ alkyl radical,
a ($C_1$-$C_6$)alkyl radical substituted with one or more radicals chosen from the following radicals: i) hydroxyl, ii) amino —$NH_2$, iii) ($C_1$-$C_6$)alkylamino, and iv) di($C_1$-$C_6$)alkylamino,
a ($C_1$-$C_6$)alkoxy radical, or
a ($C_1$-$C_6$)alkoxy radical substituted with one or more radicals chosen from the following radicals: i) hydroxyl, ii) amino, iii) ($C_1$-$C_6$)alkylamino, and iv) di($C_1$-$C_6$)alkylamino, wherein:
the compounds of formulae (I) and (II) are symmetric,
when the compound of formula (I) or (II) is cationic, it optionally comprises one or more anions $An^-$ and optionally one or more cations $M^+$ to ensure the electrical neutrality of the molecule;
wherein:
$An^-$ denoting an anion chosen from bromide, chloride, a methylsulfate ion, a toluenesulfonate ion, or a mixture thereof;
$M^+$ representing a cation chosen from sodium, potassium, magnesium, calcium, or ammonium;
wherein the compound is not one of the compounds i to viii below:

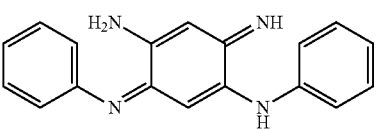

i

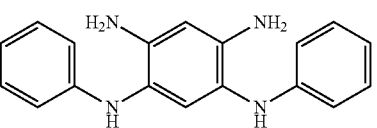

ii

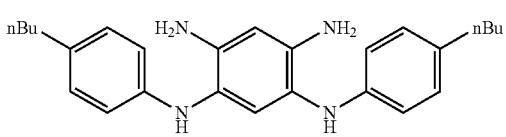

iii

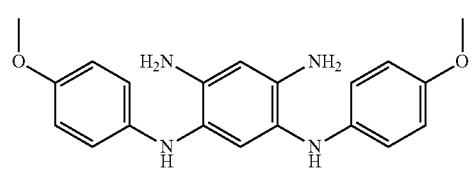

iv

v

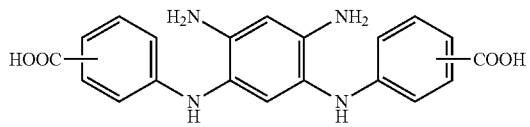

vi

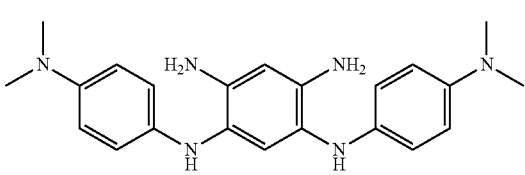

vii

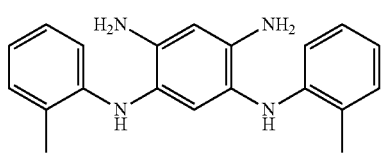

viii

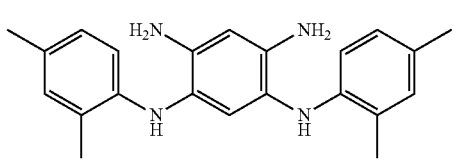

14. A cosmetic composition comprising at least one compound of claim 13.

15. The composition according to claim 14, wherein the composition does not comprise a chemical oxidizing agent.

16. The composition according to claim 14, wherein the composition further comprises at least one chemical oxidizing agent chosen from hydrogen peroxide, urea peroxide, alkali metal bromates, persalts, peracids, or oxidase enzymes.

17. A method of making a compound of formula (I) or (II) of claim 1 according to the following scheme:
access to the compounds (I):

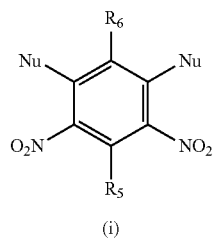 + 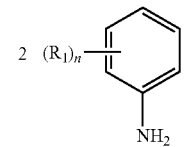 → 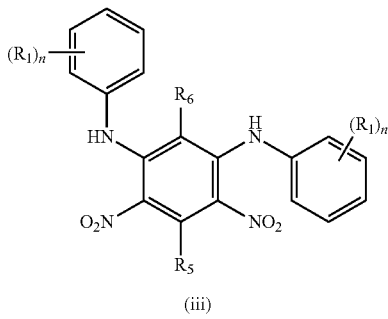

(i) (ii) (iii)

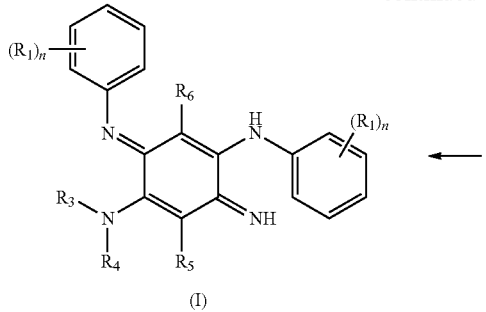

(I)

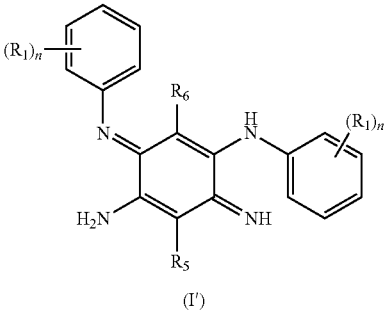

(I')

access to the compounds (II):

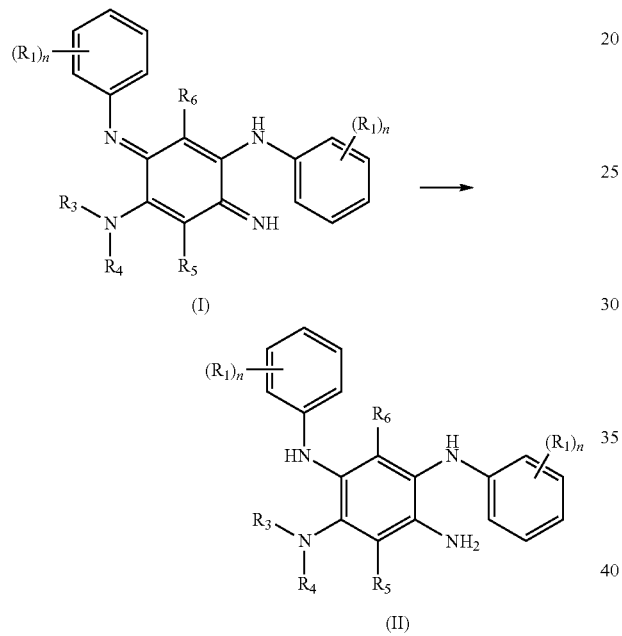

wherein the compounds of formula (I) are made by:
a) reacting one molar equivalent of 1,5-dinitrobenzene compound (i) comprising in positions 2 and 4 a nucleofugal group Nu with two molar equivalents of aniline compound (ii); Nu representing a nucleofugal group; wherein this reaction is performed i) in a polar protic solvent, ii) in the presence of one or more mineral or organic basifying agents, chosen from diisopropylethylamine, trimethylamine, sodium hydroxide, potassium hydroxide, a mineral carbonate, or an acetate, iii) and at a temperature of between 0° C. and 75° C.; and then
b) maintaining the reaction medium under stirring for a time of between 5 minutes and 48 hours; and then
c) optionally, the reaction product (iii) is optionally purified via recrystallization, filtration, or chromatography;
d) performing a reduction reaction on compound (iii); to give compound (I'); and then
f) compound (I') possibly being N-substituted with halogenated reagents $R_3$-Hal and $R_4$-Hal with Hal representing a halogen atom, to give compound (I) according to the invention after filtration, removal of the precipitate and optionally purification by chromatography or recrystallization;
g) said method comprising for the compounds (II) in performing a reduction reaction on the compounds (I).

* * * * *

UNITED STATES PATENT AND TRADEMARK OFFICE
CERTIFICATE OF CORRECTION

PATENT NO. : 11,504,318 B2
APPLICATION NO. : 16/467591
DATED : November 22, 2022
INVENTOR(S) : Stéphane Sabelle It is certified that error appears in the above-identified patent and that said Letters Patent is hereby corrected as shown below:

In the Claims

Claim 13, Column 45, Lines 33-34, please delete "prefer represents 0 or 1".

Signed and Sealed this
Seventh Day of March, 2023

*Katherine Kelly Vidal*

Katherine Kelly Vidal
*Director of the United States Patent and Trademark Office*